US008362270B2

(12) United States Patent
Makeiff et al.

(10) Patent No.: US 8,362,270 B2
(45) Date of Patent: *Jan. 29, 2013

(54) SELF-ASSEMBLED NANOSTRUCTURES

(75) Inventors: Darren Andrew Makeiff, St. Albert (CA); Rina Carlini, Oakville (CA); Hicham Fenniri, Edmonton (CA)

(73) Assignees: Xerox Corporation, Norwalk, CT (US); National Research Council of Canada, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/777,329

(22) Filed: May 11, 2010

(65) Prior Publication Data

US 2011/0282072 A1 Nov. 17, 2011

(51) Int. Cl.
C07D 235/26 (2006.01)
C07D 403/12 (2006.01)
C09D 11/02 (2006.01)

(52) U.S. Cl. ............... 548/306.4; 548/305.4; 106/31.97; 977/788

(58) Field of Classification Search ............... 548/306.4, 548/305.4; 106/31.97; 977/788
See application file for complete search history.

(56) References Cited

U.S. PATENT DOCUMENTS

| | | | |
|---|---|---|---|
| 4,073,775 A | 2/1978 | Matsuo et al. | |
| 4,138,568 A | 2/1979 | Hari et al. | |
| 5,278,020 A | 1/1994 | Grushkin et al. | |
| 5,290,654 A | 3/1994 | Sacripante et al. | |
| 5,308,734 A | 5/1994 | Sacripante et al. | |
| 5,344,738 A | 9/1994 | Kmiecik-Lawrynowicz et al. | |
| 5,346,797 A | 9/1994 | Kmiecik-Lawrynowicz et al. | |
| 5,364,729 A | 11/1994 | Kmiecik-Lawrynowicz et al. | |
| 5,370,963 A | 12/1994 | Patel et al. | |
| 5,403,693 A | 4/1995 | Patel et al. | |
| 5,418,108 A | 5/1995 | Kmiecik-Lawrynowicz et al. | |
| 5,679,138 A | 10/1997 | Bishop et al. | |
| 6,706,864 B1 | 3/2004 | Vincent et al. | |
| 7,160,380 B2 | 1/2007 | Maeta et al. | |
| 7,312,011 B2 | 12/2007 | Patel et al. | |
| 7,335,453 B2 | 2/2008 | Sacripante et al. | |
| 7,358,022 B2 | 4/2008 | Farrugia et al. | |
| 7,371,870 B2 | 5/2008 | Hosaka et al. | |
| 7,402,371 B2 | 7/2008 | Sacripante et al. | |
| 7,419,753 B2 | 9/2008 | Vanbesien et al. | |
| 7,425,398 B2 | 9/2008 | Nosella et al. | |
| 7,429,443 B2 | 9/2008 | Patel | |
| 7,442,740 B2 | 10/2008 | Patel et al. | |
| 7,503,973 B1 | 3/2009 | Carlini | |
| 7,524,599 B2 | 4/2009 | Vanbesien et al. | |
| 7,547,499 B2 | 6/2009 | Veregin et al. | |
| 7,563,318 B1 | 7/2009 | Faucher et al. | |
| 7,857,901 B2 | 12/2010 | Carlini et al. | |
| 7,883,574 B2 * | 2/2011 | Carlini et al. ............. | 106/496 |
| 7,905,954 B2 | 3/2011 | Carlini et al. | |
| 7,938,903 B2 | 5/2011 | Carlini et al. | |
| 7,985,290 B2 | 7/2011 | Carlini et al. | |
| 8,025,723 B2 | 9/2011 | Carlini et al. | |
| 2005/0048121 A1 | 3/2005 | East et al. | |
| 2005/0109240 A1 | 5/2005 | Maeta et al. | |
| 2005/0176726 A1 | 8/2005 | Wang et al. | |
| 2006/0063873 A1 | 3/2006 | Lin et al. | |
| 2006/0084732 A1 | 4/2006 | Shakely et al. | |
| 2007/0012221 A1 | 1/2007 | Maeta et al. | |
| 2008/0306193 A1 | 12/2008 | Allen et al. | |
| 2009/0221642 A1 * | 9/2009 | Jin et al. ............. | 514/322 |

FOREIGN PATENT DOCUMENTS

| | | | |
|---|---|---|---|
| JP | 2003081948 | * | 3/2003 |
| JP | A-2003-082256 | | 3/2003 |
| JP | A 2003-96056 | | 4/2003 |
| JP | A 2003-238842 | | 8/2003 |
| JP | A 2003-252864 | | 9/2003 |
| JP | A 2009-221266 | | 10/2009 |
| WO | WO 2006/005536 | | 1/2006 |
| WO | WO 2006/132443 | | 12/2006 |

OTHER PUBLICATIONS

E. Cole et al., "Oxidations with Lead Tetraacetate. Oxidations of Benzimidazole, Benzoxazoles, and Benzothiazoles," *Australian J. Chem.*, 1986, vol. 39, pp. 295-301.
K. Balakrishnan et al., "Effect of Side-Chain Substituents on Self-Assembly of Perylene Diimide Molecules: Morphology Control," *J. Am. Chem. Soc.*, vol. 128, pp. 7390-7398 (2006).
K. Hunger et al., "Uber die Molekul- und Kristallstruktur gelber Mono-"azo"-Pigmente," *Farbe+Lack*, vol. 88, pp. 453-458 (1982).
R. Clark et al., "Synthesis of Some Substituted Benzimidazolones," *J. Am. Chem. Soc.*, Apr. 5, 1958, vol. 80, pp. 1657-1662.
Hideki Maeta et al., "New Synthetic Method of Organic Pigment Nano Particle by Micro Reactor System," http://aiche.confex.com/aiche/s06/preliminaryprogram/abstract_40072.htm (date unknown).
E.F. Paulus, "Molecular and crystal structure of C.I. Pigment Red 208, 12514, nbutyl-2-[2-oxo-3-[N-(2-oxo-2,3-dihydro-5-benzimidazolyl)-carbamoyl]-naphthylidenhydrazino]-benzoat (PV-Rot HF2B),"; *Zeitschrift fur Kristallographie*, vol. 160, pp. 235-243 (1982).
J. van de Streek, et al., "Structures of six industrial benzimidazolone pigmerts from laboratory powder diffraction data," Acta Crystallographica Section B, Structural Science, 2009, vol. B65, pp. 200-211.

(Continued)

Primary Examiner — Golam M M Shameem
Assistant Examiner — Karen Cheng
(74) Attorney, Agent, or Firm — Oliff & Berridge, PLC

(57) ABSTRACT

An alkylated benzimidazolone compound of the formula:

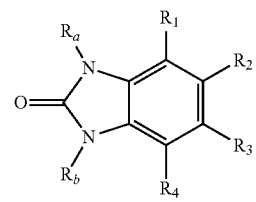

wherein at least one of $R_1$ to $R_4$ is $X$—$R_c$, where X represents a linking group, and $R_a$, $R_b$, and $R_c$ independently represents substituted or unsubstituted alkyl groups, provided that at least one of $R_a$ and $R_b$ represents H. The present disclosure provides alkylated benzimidazolone compounds and self-assembled nanostructures formed from alkylated benzimidazolone compounds.

10 Claims, 6 Drawing Sheets

OTHER PUBLICATIONS

F. H. Herbstein et al., "Crystal and Molecular Structure of 1,3-dihydro-2H-benzimidazol-2-one (the solid state tautomer of 2-hydroxybenzimidazolone)",Z. Kristallogr, vol. 173, p. 249-256 (1985).
G. M. Whitesides et al., "Engineering the Solid State with 2-Benzimidazolones",J. Am. Chem. Soc., vol. 118, p. 4018-4029 (1996).
J. de Mendoza et al, "Resorcinarenes with 2-benzimdazolone bridges: self-aggregation, self-assembled dimeric capsules, and guest complexation",Proc. Natl. Acad. Sci. USA, 99, 4962-4966 (2002).
U.S. Appl. No. 12/405,079, filed Mar. 16, 2009.
U.S. Appl. No. 12/509,161, filed Jul. 24, 2009.
U.S. Appl. No. 12/581,510, filed Oct. 19, 2009.
U.S. Appl. No. 12/581,420, filed Oct. 19, 2009.
U.S. Appl. No. 12/581,488, filed Oct. 19, 2009.
Database Registry; Chemical Abstracts Service; Columbus, Ohio; Aug. 4, 2008; XP-002610243; compounds 1038266-62-4.
Database Registry; Chemical Abstracts Service; Columbus, Ohio; Aug. 29, 2002; XP-002610244; compounds 445410-55-9.
Ebbing et al; "Resorcinarenes with 2-benzimidazolone bridges: Self-aggregation, self-assembled dimeric capsules, and guest encapsulation;" PNAS; Apr. 16, 2002; vol. 99, No. 8; pp. 4962-4966; XP-002610245.
Schweibert et al; "Engineering the Solid State with 2-Benzimidazolones;" J. Am. Chem. Soc.; May 1, 1996; vol. 118, No. 17; pp. 4018-4029; XP-002175323.
Search Report issued in European Patent Application No. 10170216.5; issued Dec. 3, 2010.
Nov. 29, 2011 Supplemental European Search Report issued in corresponding European Application No. 10170214.0.
Jan. 5, 2012 Office Action issued in U.S. Appl. No. 12/820,497.
Schulz et al., "Preparation and Characterization of Ordered Thin Films Based on Aromatic poly(1,3,4-oxadiazole)s," Reactive & Functional Polymers, vol. 30, pp. 353-360, 1996.
Cuppen et al., "Needlelike Morphology of Aspartame," Crystal Growth and Design, vol. 4, No. 5, pp. 989-997, 2004.
Winn et al., "A New Technique for Predicting the Shape of Solution-Grown Organic Crystals," AIChE Journal, vol. 44, No. 11, pp. 2501-2514, Nov. 1998.
Taulelle et al., "Pharmaceutical Compound Crystallization: Growth Mechanism of Needle-Like Crystals," Chem. Eng. Technol., vol. 29, No. 2, pp. 239-246, 2006.
Lee et al., "Controlling the Crystal Morphology of One-Dimensional Tunnel Structures: Induced Crystallization of Alkane/Urea Inclusion Compounds as Hexagonal Flat Plates," Chemical Physics Letters, vol. 307, pp. 327-332, 1999.
Chetina, "How to Grow Single Crystals for X-Ray Analysis by Solution Crystallisation," http:/www.dur.ac.ulc/crystallography.group/imagesgroup/GrowCrystals.pdf, Durham, pp. 1-16, 2009.
Apr. 24, 2012 Office Action issued in U.S. Appl. No. 12/820,497.
Feb. 23, 2012 Office Action issued in U.S. Appl. No. 13/185,058.
Mar. 9, 2012 Office Action issued in U.S. Appl. No. 13/193,326.
Mar. 9, 2012 Office Action issued in U.S. Appl. No. 13/189,887.
Mar. 22, 2012 Canadian Office Action issued in Canadian Application No. 2,717,464.
CAS Accession No. 2005:1009157 (Document No. 143:434968), Bao et al., "Behaviour of Nucleotides and Oligonucleotides in Potentiometric HPLC Detection", Analytica Chimica Acta (2005) 550(1-2), 130-136.
CAS Accession No. 2002:315164 (Document No. 136:342593), Ushio et al., WO 2002033162 A 1 (Apr. 2002).
CAS Accession No. 1950:16130 (Document No. 44:16130), Carey et al., "Relation of Chemical Constitution of a Series of Esters of Picolinic Acid to Toxicity as Insecticides", Journal of Econonic Entomology (1949), 42, 798-801.
CAS Accession No. 2004:976866 (Document No. 142:130050), Steinkamp et al., "Detection Scheme for Bioassays Based on 2,6-pyridinedicarboxylic acid Derivatives and Enzyme Amplified Lanthanide Luminescence", Analytica Chicmica Acta (2004), 526(1),27-34.
CAS Accession No. 1940:10519 (Document No. 34:10519), "Long-Chain Alkyl Derivatives of 2-aminopyridine", Journal of the Chemical Society (1939), 1855-7.
CAS Accession No. 2004:680170 (Document No. 141:197407), Sano, "Reversible Thermal Recording Material Containing Leuco Dye and Developer", JP2004230720 A (Aug. 2004).
CAS Accession No. 1980:77233 (Document No. 92:77233), Gibalewicz et al., "Study of the Electric Conductivity of Poly(vinylchloride) With Organic Additives", Polimery (Warsaw, Poland) (1979),24(9),325-9.
CAS Accession No. 1988:501769 (Document No. 109:101769), Kaneko, JP63-085548A (Apr. 1988).
CAS Accession No. 2006:889233 (Document No. 145:272901), Harashina, "Polyacetal Compositions for Prevention of Formaldehyde Release and Their Moldings", JP 2006225550 (Aug. 2006).
CAS Accession No. 1997:118989 (Document No. 126:137662), Oota, "Manufacture of Electrostatic Charge Image Development Toners by Suspension Polymerization With Uniform Size Distribution," JP08305084 (Nov. 1996).
CAS Accession No. 2005:1259726 (Document No. 144:6578), Snow et al., "Substituted N-Aryl Benzamides and Related Compounds for Treatment of Amyloid Diseases and Synucleinopathies, Their Preparation and Pharmaceutical Compostions", WO2005113489 (Dec. 2005).
CAS Accession No. 2006:597708 (Document No. 145:64647), Tsujimura et al., "Ink Sets With Good Bleeding Resistance, Ink-Jet Recording Method Using Them and Recorded Materials by The Method", JP2006160815 (Jun. 2006).
CAS Accession No. 1981:605407 (Document No. 95:605407), Pawelec et al., Benzimadazole Azo Pigments, PL105225 (Sep. 1979).
CAS Accession No. 1980:496794 (Document No. 93:96794), Fuchs, "Monoazo Dyes and Their Use", DE 2847285 (May 1980).
CAS Accession No. 1979:422411 (Document No. 91 :22411), Ciba Geigy, "Azo Pigments", JP 54029334 (Mar. 1979).
CAS Accession No. 2005:346583 (Document No. 142:393811), Shakhnovichl, "Azo Pigments for Aqueous Jet-Printing Ink Dispersion and Method for Manufacture of the Inks", US20050081749 A1 (Apr. 2005).
CAS Accession No. 2002:77478 (Document No. 136:134986), Sato et al., Japanese Patent Specification No. JP2002-030091 A (Jan. 2002).
CAS Accession No. 1999:474880 (Document No. 131 :177582), Lee et al., "Controlling the Crystal Morphology of One-Dimensional Tunnel Structures: Induced Crystallization of Alkane/Urea Inclusion Compounds as Hexagonal Flat Plates", Chemical Physics Letters (1999), 307(5,6), 327-332.
CAS Accession No. 1995:568916 (Document No. 122:291987, Boehme et al., Journal of The American Chemical Society (1995), 117(21), 5824-8.
CAS Accession No. 1977:91891 (Document No. 86:91891), Matsuo et al., Japanese Patent Specification No. JP51-134729 (Nov. 1976).
Jun. 13, 2012 Office Action issued in U.S. Appl. No. 13/185,058.
Jun. 15, 2012 Office Action issued in U.S. Appl. No. 13/193,326.
Jun. 21, 2012 Office Action issued in U.S. Appl. No. 13/189,887.
Sep. 25, 2012 Canadian Office Action issued in Canadian Application No. 2,717,579.

* cited by examiner

US 8,362,270 B2

SELF-ASSEMBLED NANOSTRUCTURES

PARTIES TO A JOINT RESEARCH AGREEMENT

This application is a result of activities undertaken within the scope of a joint research agreement between Xerox Corporation and National Research Council of Canada that was in effect on or before the date the research leading to this application was made.

CROSS-REFERENCE TO RELATED APPLICATIONS

Disclosed in U.S. patent application Ser. No. 12/405,079 filed Mar. 16, 2009, and Ser. No. 12/044,613 filed Mar. 7, 2008, both to Rina Carlini et al. is a nanoscale pigment particle composition, comprising: a benzimidazolone pigment, and a sterically bulky stabilizer compound associated non-covalently with the benzimidazolone pigment; wherein presence of the stabilizer limits an extent of particle growth and aggregation, to afford nanoscale pigment particles. Also disclosed is a process for preparing nanoscale particles of benzimidazolone pigments, comprising: providing one or more organic pigment precursor precursors to a benzimidazolone pigment comprising a benzimidazolone moiety, providing a solution or suspension of a sterically bulky stabilizer compound that associates non-covalently with the benzimidazolone moiety on one of the pigment precursors, and carrying out a chemical reaction to form a benzimidazolone pigment composition comprising nanoscale pigment particles, whereby the pigment precursors are incorporated with the benzimidazolone pigment and one or more functional moieties on the benzimidazolone pigment is non-covalently associated with the steric stabilizer, so as to limit the extent of particle growth and aggregation and result in nanoscale pigment particles.

Disclosed in U.S. patent application Ser. No. 12/509,161 filed Jul. 24, 2009, to Rina Carlini et al. is a process for preparing nanoscale particles of benzimidazolone pigments, comprising: providing one or more organic pigment precursor to a benzimidazolone pigment, providing a solution or suspension of a sterically bulky stabilizer compound that associates non-covalently with a benzimidazolone moiety on one of the pigment precursors, wherein the sterically bulky stabilizer compound is selected from the group consisting of substituted pyridine derivatives, alkylated benzimidazolone compounds, alkylated derivatives of aromatic acids, and mixtures thereof, and carrying out a coupling reaction to form a benzimidazolone pigment composition, whereby the pigment precursors are incorporated within the benzimidazolone pigment and one or more functional moieties on the benzimidazolone pigment is non-covalently associated with the sterically bulky stabilizer, so as to limit an extent of particle growth and aggregation and result in nanoscale pigment particles.

Disclosed in U.S. patent application Ser. No. 12/581,488 filed Oct. 19, 2009, to Rina Carlini et al. is a nanoscale pigment particle composition, comprising: a benzimidazolone pigment, and a sterically bulky stabilizer compound associated non-covalently with the benzimidazolone pigment, wherein the sterically bulky stabilizer compound comprises an alkylated-benzimidazolone compound; wherein the presence of the associated stabilizer limits an extent of particle growth and aggregation, to afford nanoscale pigment particles.

The entire disclosures of the above-mentioned applications are totally incorporated herein by reference.

TECHNICAL FIELD

This disclosure is generally directed to amphiphilic organic compounds with hydrogen-bonding (H-bonding) functionalities that can reversibly self-assemble into well-defined nanostructures, and methods of forming these self-assembled nanostructures. More specifically, the present disclosure relates to amphiphilic alkylated benzimidazolone compounds and self-assembled nanostructures generated therefrom. These nanostructures include a variety of different nanoparticle morphologies, often described as spherical shaped particles, planar sheets, or pseudo one-dimensional structures such as fibrils, ribbons, tapes, tubes, rods, belts, etc. Another objective of this disclosure is to provide compositions containing the above mentioned nanostructures from benzimidazolone compounds, which are either individually dispersed (e.g. free standing), or organized as building blocks to even higher order structures such as three-dimensional (3D) network (e.g., organogels or xerogels) or anisotropic materials (e.g. liquid crystals) for a wide variety of uses.

BACKGROUND

Recent technology trends in materials science indicate that the use of nanotechnology-enabled components and materials are gaining more appeal due to the enhanced (and sometimes even breakthrough) performance being exhibited. Functional nanomaterials exhibit many unique and often tunable physical and chemical properties that are different than those of their bulk counterparts. Developments have been recently made towards the fabrication of nanomaterials having well defined shape and dimensions involving either "top down" or "bottom up" fabrication strategies. "Top down" approaches involve cutting down larger structures into the desired shape with the desired dimensions (e.g. nanolithography). "Bottom up" strategies involve growing structures of the desired shape and dimensions from smaller building blocks (e.g. self-assembly). The latter is the preferred approach because it is much more efficient and bypasses the need for cost-intensive and energy-intensive fabrication processes.

Molecular self-assembly is a practical "bottom up" approach to arrive at nanostructured materials. In this approach, self-complementary molecules are designed as 'building blocks' with a specific size, shape and at least one functional group, to aggregate in an ordered manner. The resulting ensemble often possesses completely different properties than their smaller building subunits. However, the challenge of this approach is to design the appropriate molecular subunits that can assemble into useful nanostructures in a controlled manner such that the final desired size and shape can be achieved. Consequently, the modular use of hydrogen-bonding molecular building blocks is key to designing novel nanoscale supramolecular structures, non-covalent polymers, organogelators, and liquid crystals, that have useful properties for developing advanced functional materials such as for example adhesives, self-healing coatings, as well as many others.

Cyclic urea compounds that contain the benzimidazolone (BZI) functional group can self-assemble into hydrogen-bonded (H-bonded) dimer structures in the solid state resembling tapes or ribbons. These tape-like structures can vary in size and morphology depending on the type and position of functional substituents present on the benzimidazolones.

F. H. Herbstein et al., "Crystal and Molecular Structure of 1,3-dihydro-2H-benzimidazol-2-one (the solid state tautomer of 2-hydroxybenzimidazolone)", *Z. Kristallogr*, vol. 173, p. 249-256 (1985), describes the crystal structure of 1,3-dihydro-2H-benzimidazol-2-one. Ribbons of antiparallel keto-tautomer molecules linked by a zigzag set of (N—H)—(O=C) donor-acceptor pairs of hydrogen bonds are formed. The ribbons are planar and lie in a herring-bone pattern.

G. M. Whitesides et al., "Engineering the Solid State with 2-Benzimidazolones", *J. Am. Chem. Soc.*, vol. 118, p. 4018-4029 (1996), describe the solid state structures of six 2-benzimidazolone derivatives, disubstituted in the 4 and 5 positions on the benzene ring. 2-Benzimidazolones having either methyl, chlorine, and bromine atoms at the 4 and 5 positions form tapes, which pack differently than 2-benzimidazolones with hydrogens in the same positions. In contrast, three-dimensional networks were formed from 2-benzimidazolones having fluorine or iodine substituents at both 4 and 5 positions.

E. F. Paulus, "Molecular and crystal structure of C. I. Pigment Red 208, 12514, n-Butyl-2-{2-oxo-2,3-dihydro-5-benzimidazolyl)-carbamoyl]-naphthylidenhydrazino}-benzoate (PV-Rot HF2B)", Z. Kristal., vol. 160, p. 235-243 (1982) describes the crystal structure of azo-benzimidazolone Pigment Red 208. The pigment molecules are organized into tape-like structures. Each benzimidazolone group of the pigment molecules interacts with only one other benzimidazolone group from another neighboring pigment molecule to form a dimer assembly via a 2-point H-bonding interaction involving a carbonyl (C=O) acceptor and —(N—H) donor from each monomeric subunit. Each dimer is then further bound to two other dimers via two single-point H-bonding interactions between the benzimidazolone —(N—H) donor group and the 2-oxo-3-naphthylamido carbonyl group acceptor. The tapes have lipophilic edges and are further organized into layers in the crystal structure.

K. Hunger et al, "Über die Molekü und Kristallstruktur gelber Mono-"azo"-Pigmente", Farbe & Lack, vol. 88, p. 453-458 (1982) describes the crystal structure of a yellow azo-benzimidazolone pigment. The pigment molecules are organized into tape-like structures. Each benzimidazolone group of one pigment molecule subunit interacts with only one benzimidazolone group from another neighboring pigment molecule subunit, to form a dimer assembly via a 2-point interaction involving a carbonyl (C=O) acceptor and —(N—H) donor from each half. Each dimer is then further bound to two other dimers via two single-point H-bonding interactions between the benzimidazolone —(N—H) donor and the acetoamido carbonyl group acceptor. The tapes are packed into a zig-zag type arrangement in the crystal structure.

J. van de Streek et al, "Structures of six industrial benzimidazolone pigments from laboratory powder diffraction data", Acta Cryst., B65, p. 200-211 (2009) describes the crystal structures of six industrially produced benzimidazolone pigments modeled from X-ray powder diffraction data. The six industrial pigments exhibited five different tape-like hydrogen-bonded motifs.

Although hydrogen-bonded tape or ribbon structures have been observed in solid state X-ray crystal structures, it has not yet been demonstrated that benzimidazolones form "free-standing" nanostructures in solutions or dispersions. To our knowledge, the only microscopy studies that have been performed on self-assembled aggregates of benzimidazolone derivatives were by J. de Mendoza et al.

J. de Mendoza et al, "Resorcinarenes with 2-benzimidazolone bridges: self-aggregation, self-assembled dimeric capsules, and guest complexation", Proc. Natl. Acad. Set. USA, 99, 4962-4966 (2002) describes the synthesis and self-assembly behavior tetra-2-benzimidazolone functionalized resorcinarene compounds having various pendant alkyl groups. Self-organized structures such as micron-sized vesicles and long fibers were formed depending on the nature and length of the four pendant carbon chains attached at the bottom of each resorcinarene platform. Solvophobic effects, van der Waals interactions, and the packing of alkyl chains drive the formation of these higher order supramolecular assemblies from the capsules, as compared to the extensive hydrogen-bonded chains involving the benzimidazolone functional groups for the compounds of the present invention.

The appropriate components and process aspects of each of the foregoing may be selected for the present disclosure in embodiments thereof, and the entire disclosure of the above-mentioned references are totally incorporated herein by reference.

However, there remains a need for new and improved nanotechnology-enabled components and materials, particularly those having self-complementary functional groups which can self-assemble readily by a "bottom up" fabrication strategy to produce well-defined nanostructures and potentially higher-order network structures, that can be useful and desirable properties in developing functional materials.

SUMMARY

The present disclosure addresses these and other needs, by providing alkylated benzimidazolone compounds and self-assembled nanostructures formed from alkylated benzimidazolone compounds.

In an embodiment, the present disclosure provides an alkylated benzimidazolone compound of the formula:

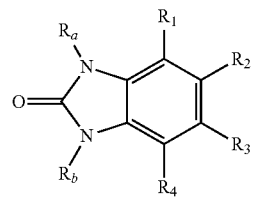

wherein at least one of $R_1$ to $R_4$ is $X$—$R_c$ where X represents a linking group, and $R_a$, $R_b$, and $R_c$ independently represents substituted or unsubstituted alkyl groups, provided that at least one of $R_a$ and $R_b$ represents H.

DETAILED DESCRIPTION OF EXEMPLARY EMBODIMENTS

Figure 1:
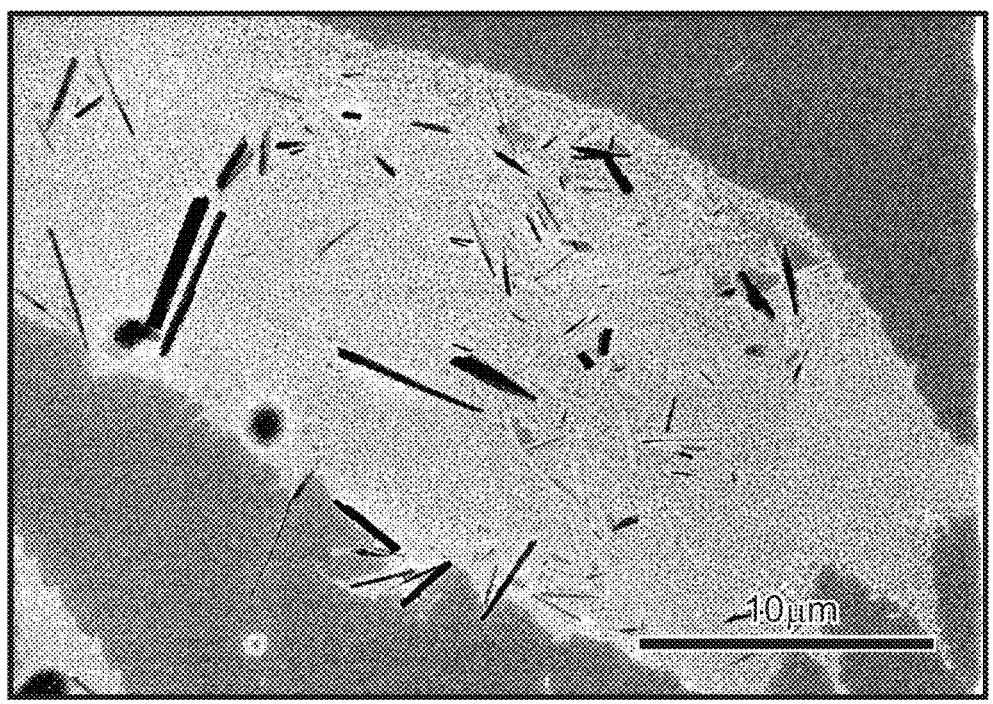
FIG. 1 shows a scanning electron micrograph of nanoscale 1D structures formed from alkylated benzimidazolone compound 2 (m=11, n=9, Table 1) in toluene (2 mg/mL).
Figure 2:
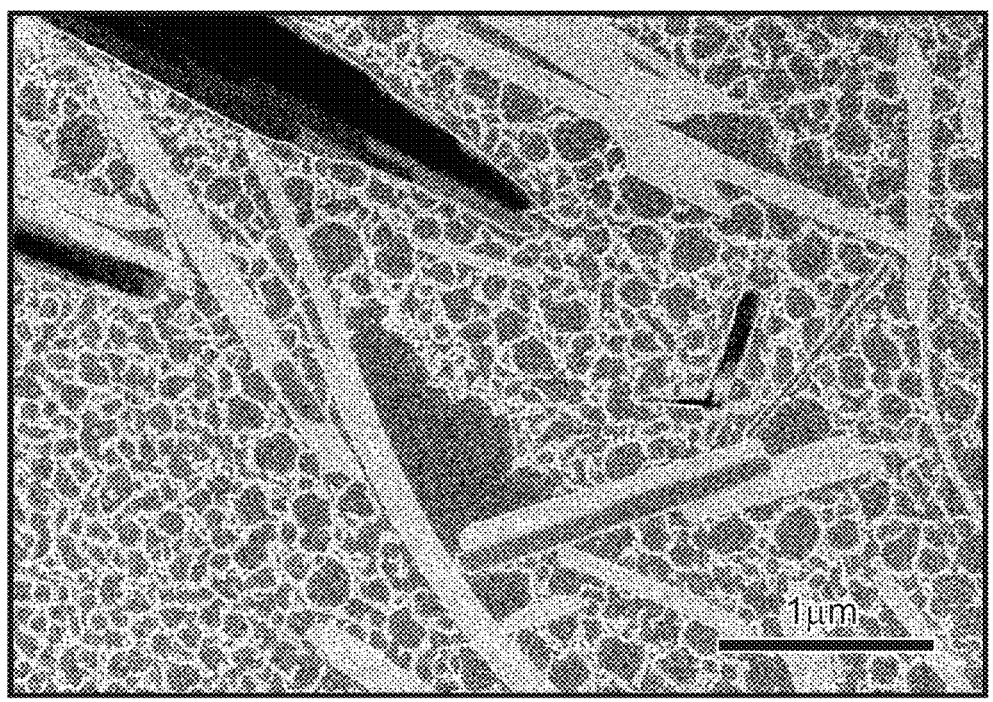
FIG. 2 shows a scanning electron micrograph of nanoscale 1D structures formed from alkylated benzimidazolone compound 2 (m=11, n=9, Table 1) in toluene (2 mg/mL).
Figure 3:
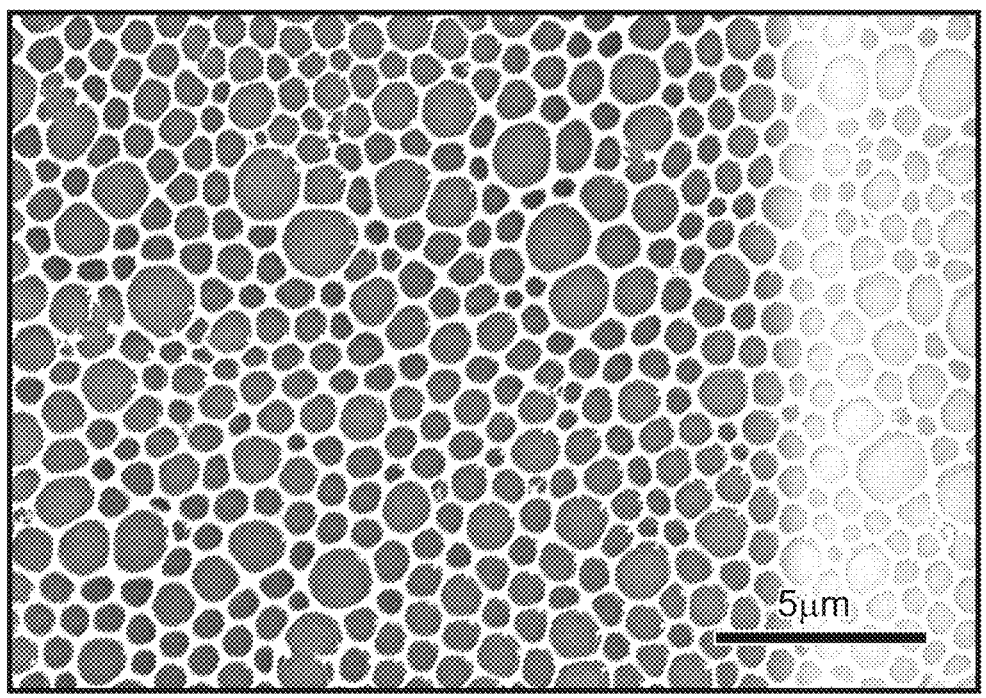
FIG. 3 shows a scanning electron micrograph of a 2D nanoscale fiber network formed from alkylated benzimidazolone compound 2 (m=7, n=5, Table 1) in chloroform (1 mg/mL).
Figure 4:
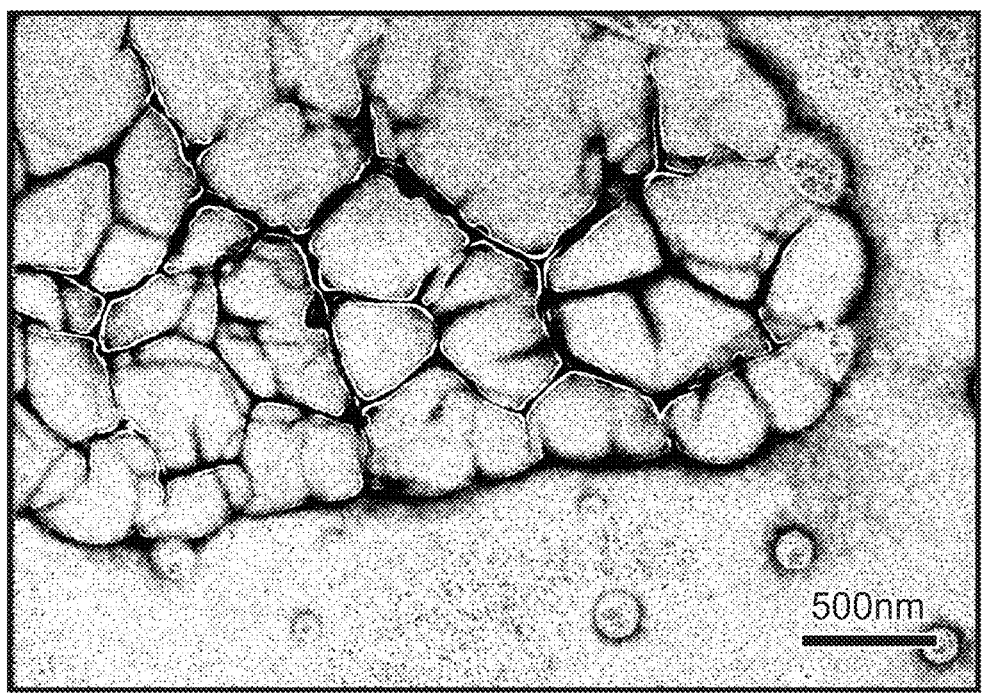
FIG. 4 shows an example of a scanning electron micrograph of nanoscale fibers (a partial 2D network) formed from alkylated benzimidazolone compound 3, Table 1 in hexanes (1.1 mg/mL).
Figure 5:
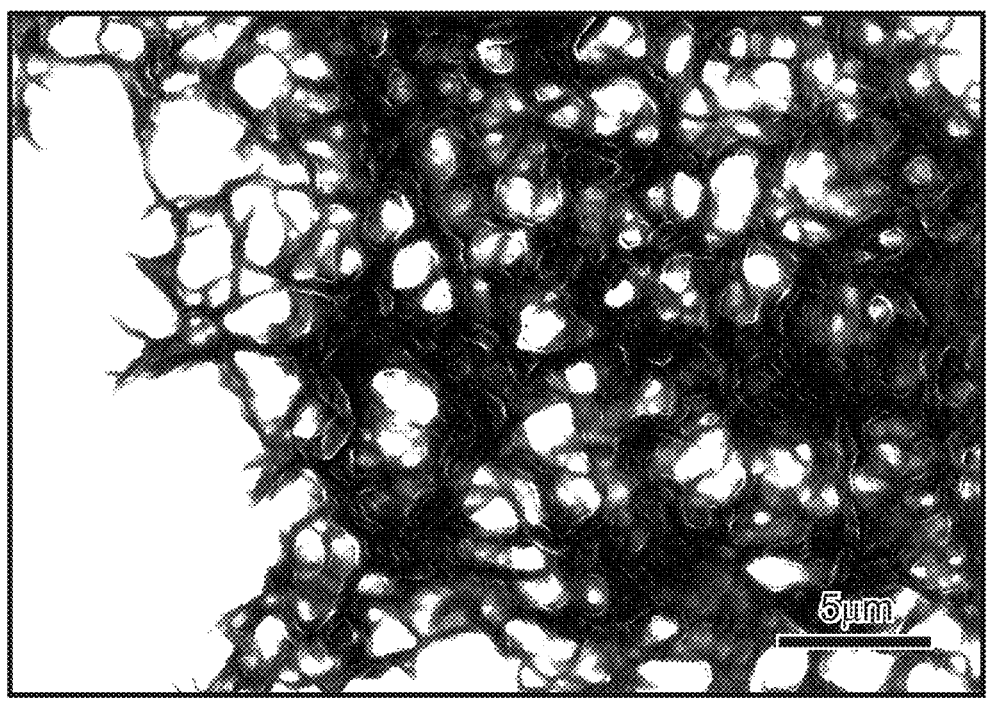
FIG. 5 shows an example of a scanning electron micrograph of an agglomerate of nanoscale fibers formed from alkylated benzimidazolone compound 3, Table 1 in toluene (1.3 mg/mL).
Figure 6:
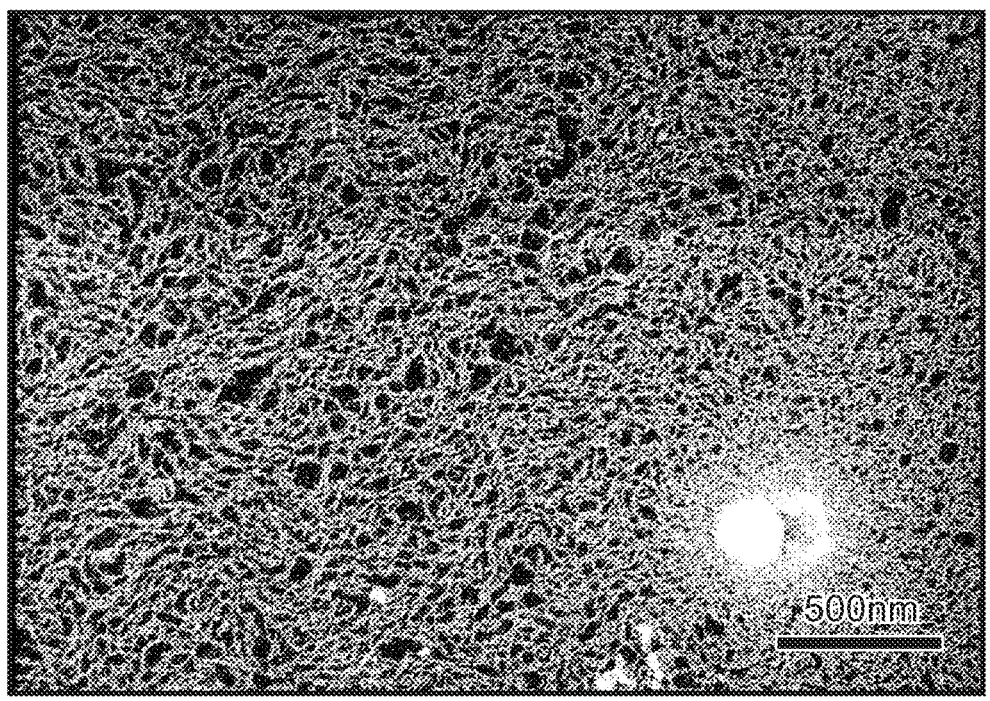
FIG. 6 shows an example of a scanning electron micrograph of fine nanoscale 1D aggregates formed from alkylated benzimidazolone compound 3, Table 1 in toluene (1.3 mg/mL).
Figure 7:
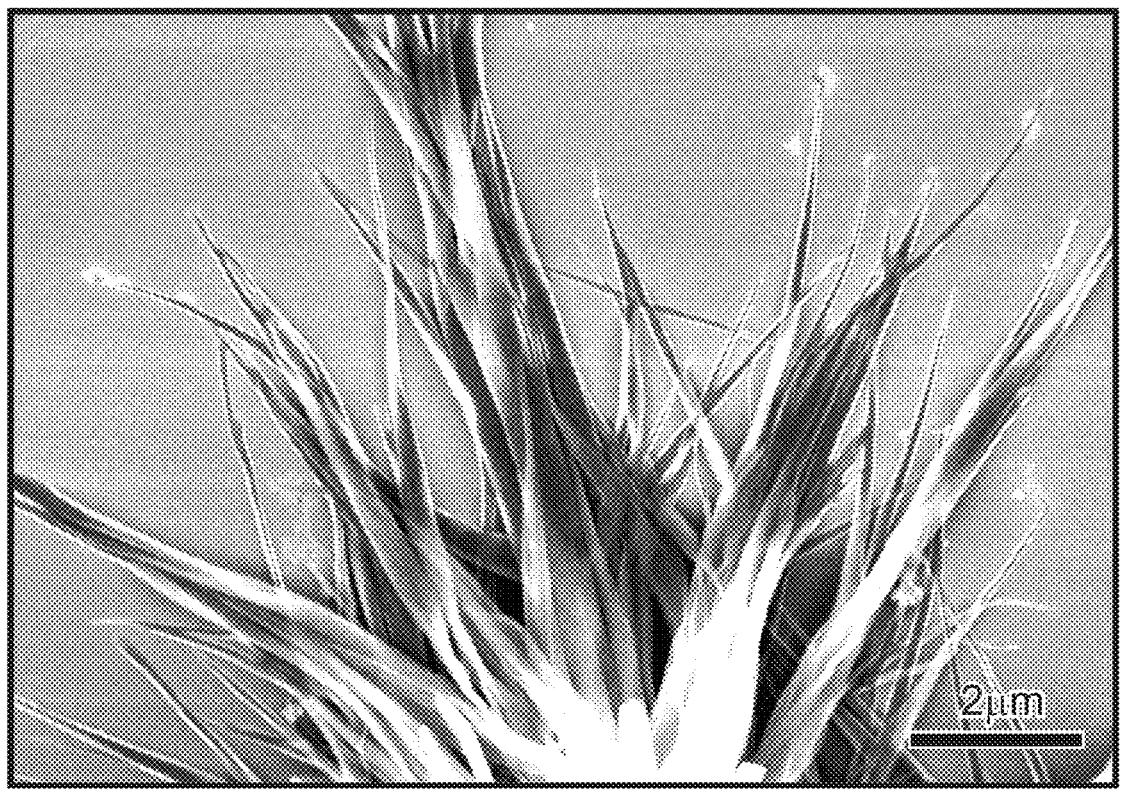
FIG. 7 shows an example of a scanning electron micrograph of nanofibers formed from alkylated benzimidazolone compound 5, Table 1 in 1-hexanol (1.3 mg/mL).
Figure 8:
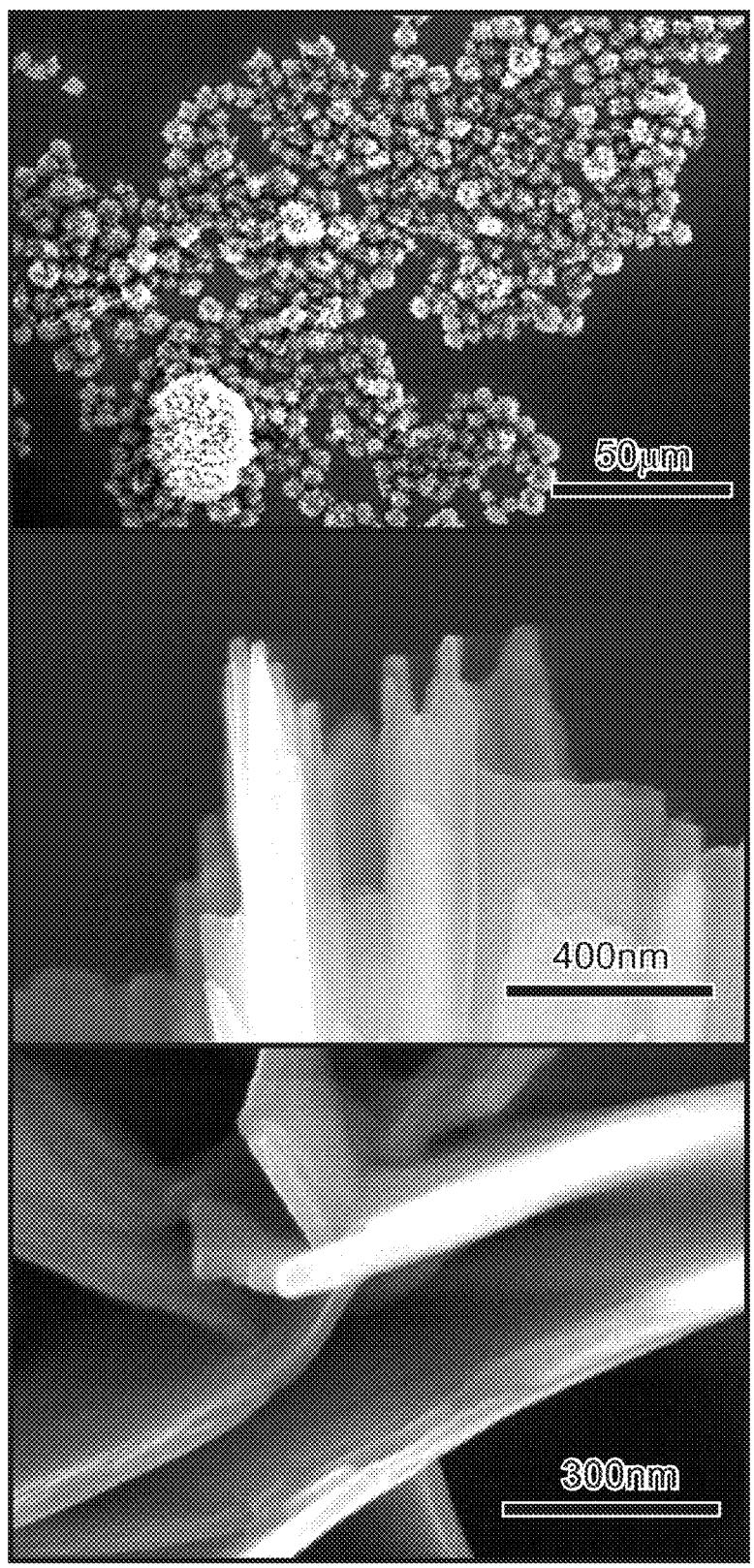
FIG. 8 shows examples of scanning electron micrographs of self-assembled nanostructures formed from alkylated benzimidazolone compound 5, Table 1 in dimethyl sulfoxide (1.2 mg/mL).
Figure 9:
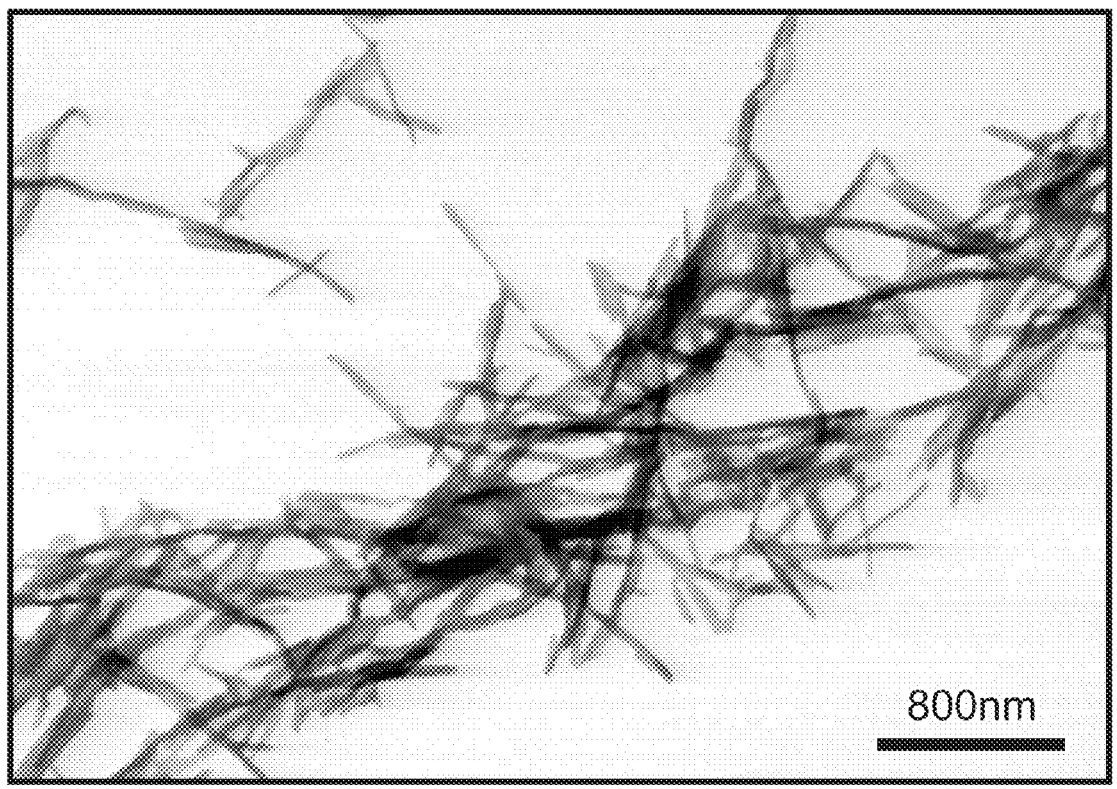
FIG. 9 shows an example of a scanning electron micrograph of nanoscale fibers formed from 5-acetoacetyl-2-aminobenzimidazolone in water.

Terms, when used in this application, have their common meaning unless otherwise stated.

The term "nanostructure" shall refer to a physical structure (e.g. a particle or the like), which, in at least one dimension, such as the smallest dimension, has a size ranging from about 1 or about 10 or about 20 to about 100 or to about 200 or to about 500 nm, such as between about 10 to about 300 nm, and which has a largest dimension that is desirably less than about 5000 nm in size, such as less than about 2000 nm in size, or less than about 1000 nanometers in size.

The term "1D structure" shall refer to a structure having a significantly larger length than height or width (or diameter). The aspect ratio, defined as length divided by the width can be at least about 5 or at least about 10, such as about 100-500. These 1D structures can thus take the form of strings (which in the case of being electrically conductive may be referred to as wires), tapes, or the like.

The term "2D structure" shall refer to a flat, planar structure having length and width that are comparable in size, but no depth (or negligible depth). The aspect ratio can be at most about 5, such as about 2, or about 1. "2D Structures" may be either porous or non porous sheet structures (e.g. a film or wafer).

The term "3D structure" shall refer to a structure that possesses the dimensions of length, width, and height that are comparable and appreciable in relative size. In the context of this disclosure, the term "3D structure" refers to a higher order arrangement of smaller (more elementary) nanostructures; i.e. 1D structures. 3D structures may include porous networks like, for example a gel network, or even more highly ordered, less porous networks such as liquid crystals.

The term "nanofibril" shall refer to a 1D structure resembling a long slender filament or fiber with diameter desirably less than about 100 nm size, such as less than about 50 nm in size, or less than about 20 nm in size. The length of the nanofibril can range from about 20 nm up to about 5000 nm or larger.

The term "nanofiber" shall refer to a 1D structure resembling a thick filament or fiber with a diameter desirably less than about 200 nm in size, or less than about 100 nm, or about 50 nm in size. "Nanofibers" in the context of this invention may consist of a single structural element or may be composed of more than one structural element, such as a bundle of smaller "nanofibrils".

Embodiments of the present disclosure provide alkylated benzimidazolone compounds and self-assembled nanostructures formed from alkylated and substituted benzimidazolone compounds.

The alkylated benzimidazolone compounds have the function of self-assembling into larger structures, either alone or in combination with other materials. For example, the compounds can be used to self-assemble with colorant molecules to form a nanoscale pigment particle composition, such as disclosed in U.S. patent application Ser. No. 12/405,079 filed Mar. 16, 2009, incorporated by reference above. The alkylated benzimidazolone compounds may thus limit the extent of primary particle aggregation and growth, so as to produce predominantly nanoscale particles.

Generally, the alkylated benzimidazolone compounds have a hydrocarbon moiety that provides sufficient steric bulk to enable the function of the compound to regulate particle size of the aggregated structures. The hydrocarbon moiety in embodiments is predominantly aliphatic, but in other embodiments can also incorporate aromatic groups, and generally contains at least 6 carbon atoms, such as at least 12 carbons or at least 16 carbons, and not more than about 100 carbons, but the actual number of carbons can be outside of these ranges. The hydrocarbon moiety can be either linear, cyclic or branched, and in embodiments is desirably branched, and may or may not contain cyclic moieties such as cycloalkyl rings or aromatic rings. The aliphatic branches are long with at least 2 carbons in each branch, such as at least 6 carbons in each branch, and not more than about 100 carbons.

It is understood that the term "steric bulk" is a relative term, based on comparison with the size of other compounds to which the alkylated benzimidazolone compound may become non-covalently associated. In embodiments, the phrase "steric bulk" refers to the situation when the hydrocarbon moiety of the compound that participates in the hydrogen bonded, occupies a 3-dimensional spatial volume that effectively prevents the approach or association of other chemical entities. As examples, the following hydrocarbon moieties on the alkylated benzimidazolone compound in embodiments may be considered to have adequate "steric bulk" so as to enable the compound to limit the extent of self-assembly or aggregation and mainly produce nanoscale structures:

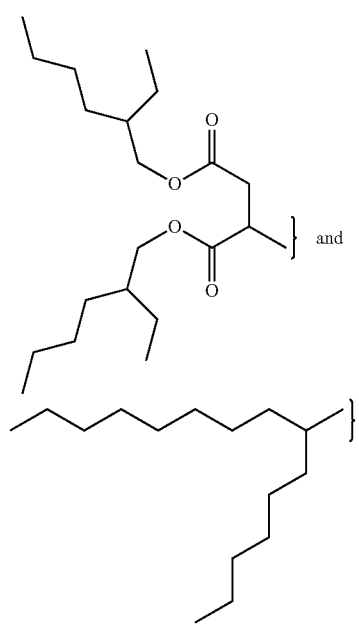

Suitable alkylated benzimidazolone compounds are desirably those that are amphiphilic; that is, they have a hydrophilic or a polar functional group with available heteroatoms for H-bonding with target molecules, as well as a non-polar or hydrophobic sterically bulky group that has at least 6 carbons and not more than 100 carbons and is predominantly aliphatic (linear, branched or cyclic) groups but can include some ethylenically unsaturated groups and/or aryl groups.

Representative examples of suitable alkylated benzimidazolone compounds include (but are not limited to) compounds of the following general Formula:

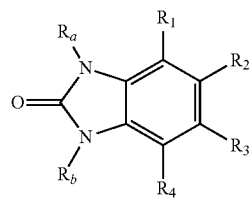

wherein $R_a$ and $R_b$ independently represent H or substituted or unsubstituted alkyl groups, provided that at least one of $R_1$, $R_2$, $R_3$, and $R_4$ is X—$R_c$, where X represents a linking group, and $R_c$ represents a substituted or unsubstituted alkyl group, provided that at least one of $R_a$ and $R_b$ represents H. The remaining groups $R_1$, $R_2$, $R_3$, and $R_4$ that are not X—$R_c$ may be the same or may be different and are not particularly limited, and can represent H or substituted or unsubstituted organic groups, such as H, a substituted or unsubstituted alkyl group, a substituted or unsubstituted aryl group, a substituted or unsubstituted aryl-alkyl group, a substituted or unsubstituted alkyl-aryl group, or the like, where the substitutions can be, for example, hydrocarbon groups, substituted hydrocarbon groups, heteroatoms, halogens, or the like. In one embodiment, at least $R_2$ represents X—Rc. In another embodiment, when $R_a$, $R_b$, $R_1$, $R_3$ and $R_4$ all represent H, and $R_2$ represents X—$R_c$ where X represents —NH—, then $R_c$ represents a substituted or unsubstituted alkyl group, such as a group other than an acylaceto group such as an acetoacetyl group.

The linking group X can be any suitable functional group that connects the substituted or unsubstituted alkyl group $R_c$ to the benzimidazolone moiety. Examples of suitable linking groups include —O—, —NH—, —S—, amide groups (—NH—(C=O)—) and (—(C=O)—NH—), amine groups (—NH—), urea groups (—NH—(C=O)—NH—), carbamate or urethane groups (—NH—(C=O)—O—) and (O—(C=O)—NH—), carbonate groups, and ester groups (—(C=O)—O—) or (—O—(C=O)—).

The groups $R_a$, $R_b$, and/or $R_c$ can be any suitable alkyl group that can provide a sterically bulky layer when the compounds are structurally aggregated, thereby preventing or limiting the approach of other particles or molecules that leads to uncontrolled aggregation and particle growth. Examples of suitable sterically bulky groups include the various non-polar or hydrophobic sterically bulky groups described previously. Specific examples of the sterically bulky alkyl groups include straight or branched alkyl groups of 1 to 100, such as 1 to 50 or 6 to 30 carbon atoms, and including large linear, branched and/or cyclic aliphatic groups like those of the general formulae:

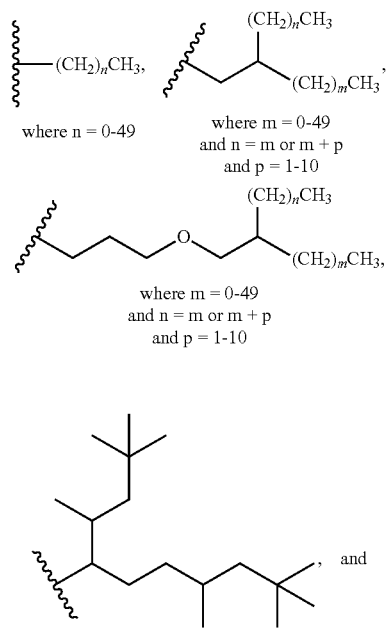

and and also includes substituted straight or branched alkyl groups of 1 to 50, such as 1 to 40 or 6 to 30 carbon atoms, including those of the formula —CO—$(CH_2)_n$—$CH_3$, where n is from 0 to 30; and the like. Other useful $R_c$ groups may include aliphatic hydrocarbons with higher degrees of branching, cyclic hydrocarbons, as well more polar groups that contain heteroatoms such as O, S, N, including linear or branched alkyleneoxy chains such as oligo- or poly-[ethyleneglycol] and the like. Group $R_c$ can also be a difunctional moiety that bridges two or more benzimidazolone groups, as illustrated in the general formula,

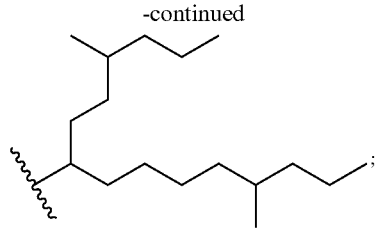

where examples of suitable difunctional groups $R_c$ include —$(CH_2)_n$—; —X—$CH_2)_nX$; —[$(XCH_2CH_2)_n$X—; —[(C=O)—$(CH_2)_n$—(C=O)]—; —X—[(C=O)—$(CH_2)_n$—(C=O)]—X—; —X—[(C=O)—X—$(CH_2)_n$—X—(C=O)]—X—; —[(C=O)—X—$(CH_2)_n$—X—(C=O)], wherein X is defined as O, S, or NH and integer n is 1 to 50; and also large branched alkylated functional groups such as:

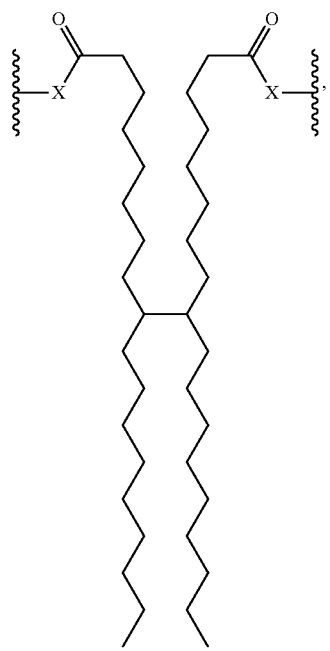

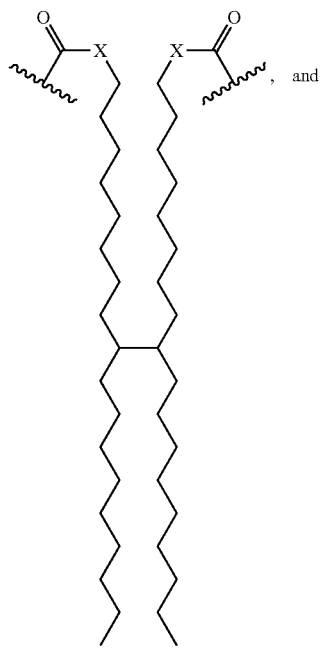

, and

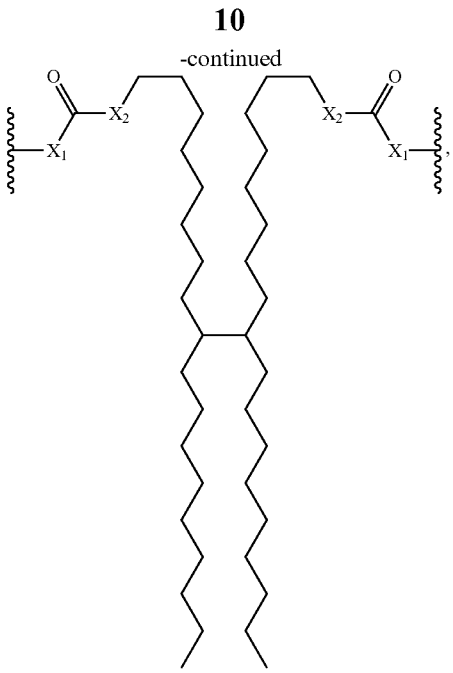

wherein X, $X_1$ and $X_2$ are defined as being either O, S, or NH, and $X_1$ and $X_2$ may or may not be the same.

Specific examples of the alkylated benzimidazolone compounds thus include, but are not limited to, those in the following Tables 1 and 2:

TABLE 1

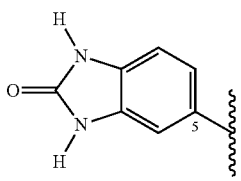 [SMILES: *c1ccc2[nH]c(=O)[nH]c2c1]

| Position 5 functional moiety | X | Sterically Bulky Group(s) $R_1$ | $R_2$ | $R_3$ |
|---|---|---|---|---|
| 1 ⸺X⸺C(O)⸺$R_1$ | NH | $(CH_2)_nCH_3$<br>n = 2, 11, 17 | — | — |
| 2 ⸺X⸺C(O)⸺$R_1$ | NH | $(CH_2)_mCH_3$ / $(CH_2)_nCH_3$ (branched)<br>m = 5, n = 3<br>m = 7, n = 5<br>m = 11, n = 9 | — | — |
| 3 ⸺X⸺C(O)⸺$R_1$ | NH | (branched alkyl structure) | — | — |

TABLE 1-continued

[Structure: benzimidazol-2-one with position 5 indicated as attachment point]

| Position 5 | | Sterically Bulky Group(s) | | |
|---|---|---|---|---|
| functional moiety | X | R₁ | R₂ | R₃ |
| 4  ⁓X—C(=O)—R₁ | NH | [branched alkyl: 3,7,11-trimethyl type structure] | — | — |
| 5  ⁓X₁—C(=O)—X₂—R₁ | X₁ = O<br>X₂ = NH | $(CH_2)_n CH_3$<br>n = 11, 17 | — | — |
| 6  ⁓X₁—C(=O)—X₂—R₁ | X₁ = O<br>X₂ = NH | $(CH_2)_n CH_3$<br>n = 11, 17 | — | — |
| 7  ⁓X(R₁)(R₂) | N | H | $(CH_2)_n CH_3$<br>n = 1, 17 | — |
| 8  ⁓X(R₁)(R₂) | N | H | ⁓[CH(CH₃)—O]ₙ—$(CH_2)_m CH_3$<br>m = 3, n = 2<br>m = 3, n = 3 | — |
| 9  ⁓X(R₁)(R₂) | N | $(CH_2)_n CH_3$<br>n = 3, 11, 17 | $(CH_2)_n CH_3$<br>n = 3, 11, 17 | — |
| 10  ⁓X(R₁)(R₂) | N | ⁓[CH(CH₃)—O]ₙ—$(CH_2)_m CH_3$<br>m = 3, n = 2<br>m = 3, n = 3 | ⁓[CH(CH₃)—O]ₙ—$(CH_2)_m CH_3$<br>m = 3, n = 2<br>m = 3, n = 3 | — |
| 11  ⁓X(R₁)(R₂) | N | ⁓[O]ₙ—$(CH_2)_m CH_3$<br>m = 1, n = 3 | ⁓[O]ₙ—$(CH_2)_m CH_3$<br>m = 1, n = 3 | — |
| 12  ⁓X⁺(R₁)(R₂)(R₃) | N | $(CH_2)_n CH_3$<br>n = 1, 17 | $(CH_2)_n CH_3$<br>n = 1, 17 | $(CH_2)_n CH_3$<br>n = 1, 17 |

TABLE 1-continued

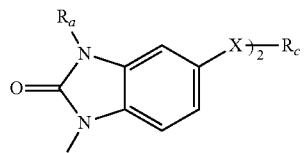

| Position 5 | | Sterically Bulky Group(s) | | |
| --- | --- | --- | --- | --- |
| | functional moiety | X | R$_1$ | R$_2$ | R$_3$ |
| 13 | (R$_3$, R$_2$, X$^\oplus$, R$_1$) | N | (O, (CH$_2$)$_m$CH$_3$)$_n$ <br> m = 3, n = 2 <br> m = 3, n = 3 | (O, (CH$_2$)$_m$CH$_3$)$_n$ <br> m = 3, n = 2 <br> m = 3, n = 3 | (O, (CH$_2$)$_m$CH$_3$)$_n$ <br> m = 3, n = 2 <br> m = 3, n = 3 |
| 14 | (R$_3$, R$_2$, X$^\oplus$, R$_1$) | N | (O, (CH$_2$)$_m$CH$_3$)$_n$ <br> m = 1, n = 3 | (O, (CH$_2$)$_m$CH$_3$)$_n$ <br> m = 1, n = 3 | (O, (CH$_2$)$_m$CH$_3$)$_n$ <br> m = 1, n = 3 |

TABLE 2

[Benzimidazolone structure with R$_a$ and R$_b$ on the nitrogens and X$\overset{}{\underset{2}{-}}$R$_c$ substituent]

R$_a$ = R$_b$ = H

| | Group X | R$_c$ |
| --- | --- | --- |
| 1 | X$_1$—C(=O)—X$_2$ <br> X$_1$ = X$_2$ = NH | [branched long alkyl chain] |
| 2 | X$_1$—C(=O)—X$_2$ <br> X$_1$ = O <br> X$_2$ = NH | [branched long alkyl chain] |
| 3 | X$_1$—C(=O)— <br> X$_1$ = NH | [branched long alkyl chain] |
| 4 | X$_1$—C(=O)— <br> X$_1$ = O | [branched long alkyl chain] |

TABLE 2-continued

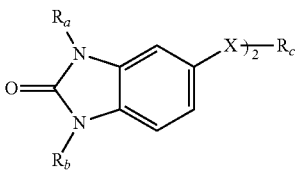

$R_a = R_b = H$

| Group X | | $R_c$ |
|---|---|---|
| 5 | 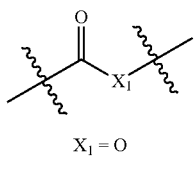<br>$X_1 = O$ | 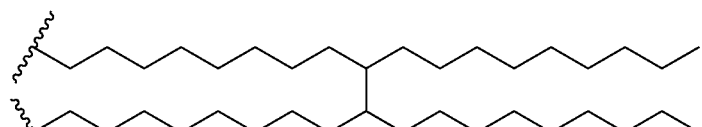 |
| 6 | 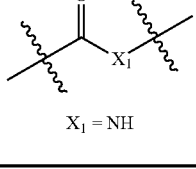<br>$X_1 = NH$ | 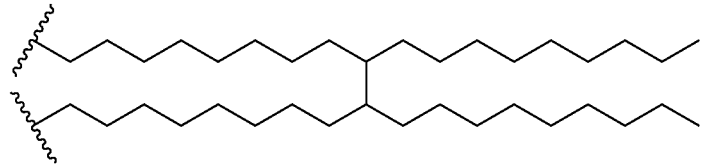 [SMILES: *CCCCCCCCC(CCCCCCCCC)C(CCCCCCCC*)CCCCCCCCC] |

The N-alkylated 5-amidobenzimidazolone compounds (such, as entries 1-4 in Table 1) are prepared from commercially available materials using any desired or effective method. For example, an alkanoic acid chloride can be reacted with 5-aminobenzimidazolone in approximately equimolar amounts at a suitable temperature, optionally in the presence of a solvent, and optionally in the presence of a base.

There are many methods for activating alkanoic acids for reactivity with nucleophiles such as amines, alcohols, etc., that are well-known and familiar to those skilled in the art. One method involves conversion of the alkanoic acid to the corresponding alkanoic acid chloride using any desired or effective method to those skilled in the art. For example, the alkanoic acid chloride may be prepared from the corresponding alkanoic acid precursor by reaction with a chlorinating reagent, typically in the presence of a solvent, and optionally in the presence of a catalyst. Suitable chlorinating reagents may include, but are not limited to, oxalyl chloride, thionyl chloride, phosphorous trichloride, or phosphorous pentachloride. Other reagents may also be used to activate the carboxylic acid for reaction with the amine, including but not limited to dicyclohexylcarbodiimide (DCC), diisopropylcarbodiimide (DIC), and benzotriazoles.

More specifically, the alkanoic acid can be reacted with oxalyl chloride in the presence of an optional catalyst at about 0 to about 5° C. in a suitable solvent. Examples of catalysts include N,N-dimethylformamide (DMF). The catalyst, when used, can be present in any desired or effective amount. In one embodiment at least about 0.1 mol percent, in another embodiment at least about 0.5 mol percent, in another embodiment at least about 1 mol percent, in another embodiment at least about 10 mol %, and yet in another embodiment at least about 20 mol % based on the amount of oxalyl chloride, although the amount can be outside these ranges.

The alkanoic acid and oxalyl chloride are present in any desired or effective relative amounts, such as about 0.8 mol to about 3.0 mol of oxalyl chloride per every mol of alkanoic acid, or about 1.0 mol to about 2.0 mol of oxalyl chloride per every mol of alkanoic acid, or about 1.2 mol to about 1.5 mol of oxalyl chloride per every mol of alkanoic acid, although the relative amounts can be outside of these ranges.

Subsequent to the reaction between the alkanoic acid and oxalyl chloride, the first reaction product need not be recovered; the reaction mixture can be appropriately mixed with an amino-benzimidazolone such as a 5-amino-benzimidazolone, along with the addition of solvent and base if desired, to complete the reaction. Alternatively, the first reaction product alkanoic acid chloride may be isolated prior to mixing with 5-aminobenzimidazolone, along with the addition of an optional solvent and base if desired to complete the reaction. The first reaction product and 5-amino-benzimidazolone can be present in any desired or effective relative amounts, such as about 0.8 mol to about 1.1 mol, or about 1.0 mol, of the first reaction product per every mol of 5-aminobenzimidazolone, although the relative amounts can be outside of these ranges.

N-Alkylated 5-ureidobenzimidazolones, as in entry 5 in Table 1 and entry 1 in Table 2, can be prepared by conventional methods from alkylisocyanate reactants by any desired or effective method. For example, 5-aminobenzimidazolone can be reacted with a desired alkylisocyanate of the formula OCN—$R_1$ in approximately equimolar amounts at a specified temperature, optionally in the presence of a solvent. Thereafter the resulting product is obtained in very high purity simply by precipitation with water, followed by washing and drying.

The alkylisocyanate and 5-aminobenzimidazolone can be present in any desired or effective relative amounts, such as in one embodiment about 0.4 mol to about 1.4 mol, or about 0.6 mol to about 1.2 mol, or about 0.8 mol to about 1.0 mol of the first reaction product per every mol of 5-aminobenzimidazolone, although the relative amounts can be outside of these ranges.

O-Alkylated carbamates or urethanes, such as entry 8 in Table 1 can be prepared readily by reaction of 5-hydroxybenzimidazolone with an alkyl isocyanate or polyisocyanate, such as octadecyl isocyanate or the diisocyanate derivative of C-36 dimer acid (obtained from Henkel Corp. as DDI 1410™), in the presence of a catalytic amount of a Lewis Acid catalyst, such as for example dibutyltin dilaurate, and with mild heating. The reactant 5-hydroxybenzimidazolone can be prepared by various methods reported previously in the literature, which are totally incorporated herein by reference, such as for example U.S. Patent Application No. 2005/

0176726 involving demethylation of 5-methoxybenzimidazolone, or as described in *Australian J. Chem.*, 1986, 39(2), 295-301 by the over-oxidation of benzimidazole with lead tetraacetate, or by the methods reported in *J. Am. Chem. Soc.* 1958, 80, 1657-1662 and in. U.S. Pat. No. 4,138,568, which describe the reaction between 5-hydroxy-1,2-phenylene diamine with phosgene in aqueous hydrochloric acid or molten urea gives 5-hydroxybenzimidazolone in good yields.

The alkylisocyanate and 5-hydroxybenzimidazolone can be present in any desired or effective relative amounts, such as about 0.4 mol to about 1.4 mol or about 0.6 or about 0.8 to about 1.0 or about 1.2 mol of the first reaction product per every one mol of 5-hydroxybenzimidazolone, although the relative amounts can be outside of these ranges.

Examples of suitable catalysts include (but are not limited to) Lewis acid catalysts such as dibutyl tin dilaurate, bismuth tris-neodecanoate, cobalt benzoate, lithium acetate, stannous octoate, triethylamine, ferric chloride, aluminum trichloride, boron trichloride, boron trifluoride, titanium tetrachloride, tin tetrachloride, and the like. The catalyst, when present, can be present in any desired or effective amount, such as at least about 0.2 mole percent, at least about 0.5 mole percent, or at least about 1.0 mole percent, but desirably no more than about 10 mole percent, or no more than about 7.5 mole percent, or no more than about 5.0 mole percent, based on the amount of isocyanate, although the amount can be outside these ranges.

The substituted amino or ammonium groups at position 5 of the benzimidazolone compounds, such as in entries 12-14 of Table 1, can also be produced in one step by an alkyl substitution reaction (or, alkylation reaction) between 5-aminobenzimidazolone and 1.0-3.0 molar equivalents of a suitable alkylating reagent such as an alkyl halide, wherein the halogen is selected from F, Cl, Br, I; or a suitable alkyl ester of an alkanesulfonate or arenesulfonate reagent such as alkyl methanesulfonates (commonly known as alkyl mesylates, or alkyl para-toluenesulfonates (commonly known as alkyl tosylates), or alkyl trifluoromethanesulfonate (commonly known as alkyl triflates) wherein the corresponding leaving group is the mesylate, tosylate or triflate anion; or, a suitable alkyl ester of a carboxylic acid, such as alkyl acetate, alkyl formate, alkyl propionate and the like, wherein the leaving group that is displaced is the acetate, formate, propionate, etc.

The alkylating agent and 5-aminobenzimidazolone can be present in any desired or effective relative amounts, such as about 0.4 to about 1.4 mol or about 0.6 to about 1.2 mol or about 0.8 to about 1.0 mol of the first reaction product per every one mol of 5-aminobenzimidazolone, although the relative amounts can be outside of these ranges.

Examples of suitable catalysts include but are not limited to halide salts such as potassium iodide or sodium iodide, and the like. The catalyst, when present, can be present in any desired or effective amount, such as at least about 20 mole percent, at least about 50 mole percent, or at least about 100 mole percent, but desirably no more than about 100 mole percent, or no more than about 75 mole percent, based on the amount of alkylating reagent, although the amount can be outside these ranges.

Other alkylated benzimidazolone compounds, including those shown in Tables 1 and 2 and compounds similar thereto, can be made by similar reaction schemes. Such additional alkylated benzimidazolone compounds are also within the scope of the present disclosure.

The types of non-covalent chemical bonding that can occur between separate molecules of the alkylated benzimidazolone compounds, or between the alkylated benzimidazolone compounds and other compounds, are, for example, van der Waals forces, ionic or coordination bonding, H-bonding, and/or aromatic pi-stacking bonding. In embodiments, the non-covalent bonding is predominately H-bonding and van der Waals' forces, but can include aromatic pi-stacking bonding as additional or alternative types of non-covalent bonding between the respective molecules.

The organic nanostructures from the alkylated. BZI compounds described herein can be prepared, for example, by homogeneously mixing a self-assembling, alkylated BZI derivative having the above formula with a polar or nonpolar liquid under conditions sufficient to effect the extent of dissolution and self-assembly, usually by heating followed by subsequent cooling and aging for a given period of time to allow the desired nanostructures to fully mature. Mixing of the components may be conducted at temperatures ranging between room temperature and the boiling point of the liquid. The self-assembling, alkylated BZI compound may be added in the form of powder particles, which may completely dissolve in the liquid to form a clear solution or may only partially dissolve to form a dispersion. Alternatively the self-assembling, alkylated BZI compound may be added as a solution dissolve in a suitable solvent including both polar and nonpolar liquids. This liquid that the alkylated BZI compound is dissolved in may be the same as the liquid it is being added to, or may be a different liquid. In addition, the liquid to which the solution of alkylated BZI compound is being added to may be a good or poor solvent for the alkylated BZI compound and resulting self-assembled nanostructures. The nanostructure compositions of the present invention may also be formed, for example, at elevated temperatures by dissolving or dispersing the self-assembling alkylated BZI compound in the liquid at elevated temperatures, and thereafter cooling the resulting solution to a lower temperature, whereby a colloid solution or dispersion of nanostructured aggregates forms while aging for a suitable period of time.

According to the present disclosure, the self-assembling alkylated BZI compound may be present in a wide range. Preferred is a range of about 0.05% to 20% by weight based upon the liquid of the composition, more preferably 0.075 to 10%, and even more preferably 0.1 to 1.5 to 2.0%. The properties of the compositions containing the nanostructures may be controlled depending on the kind and amount of alkylated BZI compound added. A suitable amount of alkylated BZI compound may be readily determined by routine experimentation and will vary with the desired physical property of the composition and other components therein. As is understood by those skilled in the art, a lower amount of alkylated BZI compound often makes the compositions more desirable, inasmuch as the non-assembled, individual alkylated BZI molecules may often demonstrate chemical and physical properties that are different from the end use properties of the compositions containing self-assembled nanostructures from alkylated benzimidazolone compounds.

More than one self-assembling BZI compound may be utilized to form nanostructures in a particular liquid. For example, a mixture of two different isomers or homologues of a particular alkylated BZI compound (e.g., different linkages, organic substituents, etc.) may be used.

When preparing the self-assembled nanostructures in accordance with the process of this invention, the requisite amount of alkylated BZI is mixed with the liquid and the materials are blended, for example under ambient conditions of temperature and pressure. Different temperatures and pressures may be utilized in the mixing process where, for example, loss of vapors, in the case of a low-boiling liquid hydrocarbon, is to be avoided (use lower temperatures and/or higher pressures) or when easier mixing, in the case of higher-boiling liquids, is to be obtained (use higher temperatures and/or lower pressures).

The components may be mixed by any means such as stirring, shaking, or passing the mixtures through a homogenizer, or subjecting to ultrasonic waves to produce a homogeneous composition. Regardless of the method of blending, self-assembled nanostructures are produced as a result of obtaining a solution or dispersion of the alkylated BZI compound in the liquid.

The compositions of self-assembled nanostructures of the present disclosure, once formed, may be contained in liquid or in solid form upon evaporation of the liquid. Liquid compositions may vary, and consist of clear or turbid colloidal solutions, opaque dispersions, settled precipitates, clear viscous (supramolecular) polymer solutions, or thick gels. The viscosity of liquid compositions of the nanostructures varies from thin, pourable type to a shape retaining material (i.e., a gel). The resulting nanostructures may be robust, individually dispersed, or highly cohesive, and are stable in storage for variable periods (depending on the alkylated BZI compound, its concentration, the liquid, and the temperature of storage), thermally reversible, and are sheer stress thinnable.

The self-assembled nanostructures made from the alkylated benzimidazolone compounds described herein generally comprise the alkylated benzimidazolone compounds in a major, predominant, substantial, or entire amount of the solid form of the nanostructure. That is, in embodiments, the solid portion of the nanostructures (not including any solvent or liquid carrier that may be included) comprises, consists essentially of, or consists of the alkylated benzimidazolone compounds. Of course, two or more different alkylated benzimidazolone compounds can be included, as desired. Thus, in embodiments, the nanostructures do not contain other hydrogen-bonding materials such as steric stabilizers, and do not correspond to nanoparticles that may be formed by association of the alkylated benzimidazolone compounds with pigment particles.

However, in other embodiments, the nanostructure may comprise one or more additives, such as to provide desired properties to the nanostructure. For example, the additives may provide such properties as hardness, rigidity, porosity, color, or the like to the nanostructure. Such additives in embodiments do not hydrogen bond to the alkylated benzimidazolone compounds in the nanostructure. Instead, in these embodiments, the additives can be covalently or ionically bound to the nanostructure, or they can be mixed, dispersed, or the like in the nanostructure.

A number of characterization methods are useful for detecting and characterizing self-assembled nanostructures from alkylated BZI compounds. The simplest test is to observe any changes in viscosity (rheology) of the liquid containing the alkyl BZI compound relative to the neat liquid alone. A highly viscous fluid or jelly-like material strongly suggests the formation of nanostructured supramolecular aggregates (i.e., supramolecular polymers or gels). If the mixture does not flow under the influence of gravity upon inversion of the sample vial, then the mixture is considered to be a gel. The increase in viscosity and gelation of liquids is known to occur due to the presence and entanglement of long, 1D aggregates.

Microscopy techniques such as optical light microscopy, scanning electron microscopy (SEM), transmission electron microscopy (TEM), atomic force microscopy (AFM)/scanning probe microscopy (SPM), and fluorescence microscopy are useful for determining the size and morphology of the nano (and microstructures formed from alkylated BZI compounds. Samples are typically prepared by depositing a drop of the liquid composition containing the nanostructures onto an appropriate sample substrate such as a carbon film coated copper mesh TEM grid, removing the excess liquid by blotting with filter paper, and then allowing to dry prior to analysis. Dynamic light scattering is also useful for detecting the presence of particles between 1 nm and 1 µm in size, measuring the size/size distribution of the dispersed particles. Rheometry is useful for determining the viscoelastic properties and thermal phase transitions for compositions of the self-assembled nanostructures. X-ray diffraction is useful for characterizing the structure of the self-assembled nanostructures size as phase identification, crystallinity, phase transitions, crystal structure refinement and determination, and size and strain broadening of crystallite nanostructures. NMR spectroscopy is useful in detecting the formation intermolecular noncovalent interactions stabilizing the nanostructures, their diffusion properties, as well as phase transitions. UV-Vis can be used for detecting the presence of nanostructures as well as confirming the presence of intermolecular pi-stacking interactions. FT-IR spectroscopy is also useful for the detection of hydrogen-bonding interactions involved in stabilizing the self-assembled nanostructures. Differential Scanning Calorimetry (DSC) is another useful characterization technique, which enables the identification of thermal phase transitions within the compositions containing the nanostructures.

As disclosed in U.S. patent application Ser. No. 12/405,079, the alkylated benzimidazolone compounds can be used for making nanoscale particles of azo-benzimidazolone organic pigments, by using a bottom-up assembly synthetic approach that makes use of the alkylated benzimidazolone compounds as amphiphilic surface auxiliaries for controlling the particle size, morphology, dispersion properties and even coloristic properties of the resulting nanopigments. The procedures disclosed therein can be used to make other suitable nanopigments and nanocolorants.

The alkylated benzimidazolone compounds, and self-assembled structures made from those compounds, can be used in a wide variety of applications. For example, the alkylated benzimidazolone compounds can be used as organogelators in the formation of organogels, which may then be used as thickening agents for numerous products such as paints, inks, coatings, lubricants, adhesives, personal care products, pharmaceutical and dermatological gels, and even in certain food products, or they can be used in tissue engineering, biomineralization (as templates), catalysis, gel-based scaffolds for energy transfer and light harvesting, and the like. The alkylated benzimidazolone compounds can also be used in the formation of novel hydrogen bonded liquid crystal materials, where the liquid crystal material can comprise the alkylated benzimidazolone compounds disclosed herein themselves, or in combination with another complementary H-bonding molecules or polymers with pendant complementary H-bonding groups.

The alkylated benzimidazolone compounds, and self-assembled structures made from those compounds, can also be used in combination with coloring agents in a variety of ink and coating compositions, such as in liquid (aqueous or non-aqueous) printing ink vehicles, including inks used in conventional pens, markers and the like, liquid inkjet ink compositions, solid or phase change ink compositions, paints and automotive coatings, and the like. For example, the compounds can be formulated into a variety of ink vehicles, including solid and phase-change inks with melt temperatures of about 60 to about 130° C., solvent-based liquid inks or radiation-curable such as UV-curable liquid inks, and even aqueous inks.

In addition to ink compositions, the compounds can be used in combination with coloring agents in a variety of other applications, such as for paints, resins and plastics, lenses, optical filters, and the like according to applications thereof. By way of example only, the compounds can be used for toner compositions, which include polymer particles and pigment particles, along with other compounds that are formed into toner particles and optionally treated with internal or external additives such as flow aids, charge control agents, charge-enhancing agents, filler particles, radiation-curable agents or particles, surface release agents, and the like. Toner compositions can be prepared by a number of known methods including extrusion melt blending of the toner resin particles, pigment particles and other colorants and other optional additives, followed by mechanical comminution and classification. Other methods include those well known in the art such as spray drying, melt dispersion, extrusion processing, dispersion polymerization, and suspension polymerization. Further, the toner compositions can be prepared by emulsion/aggregation/coalescence processes, as disclosed in references U.S. Pat. Nos. 5,290,654, 5,278,020, 5,308,734, 5,370,963, 5,344,738, 5,403,693, 5,418,108, 5,364,729, 5,346,797, 7,547,499, 7,524,599, 7,442,740, 7,429,443, 7,425,398, 7,419,753, 7,402,371, 7,358,022, 7,335,453, and 7,312,011, the entire disclosures of which are incorporated herein by reference. The toner particles can in turn be mixed with carrier particles to form developer compositions. The toner and developer compositions can be used in a variety of electrophotographic printing systems.

Examples are set forth herein below and are illustrative of different compositions and conditions that can be utilized in practicing the disclosure. All proportions are by weight unless otherwise indicated. It will be apparent, however, that the disclosure can be practiced with many types of compositions and can have many different uses in accordance with the disclosure above and as pointed out hereinafter.

EXAMPLES

Example 1

Synthesis of 5-(2'-decyltetradecanamido)-2-benzimidazolone (compound #2 (m=11, n=9), Table 1)

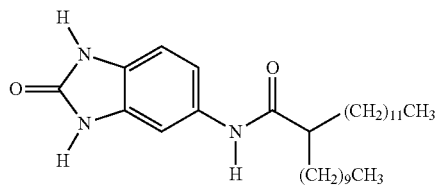

Step I—Synthesis of 2-decyltetradecanoyl chloride

2-Decyltetradecanoic acid (ISOCARB 24, obtained from Sasol America, Texas, 7.09 g, 0.0192 mol) and dry tetrahydrofuran (THF, 100 mL) are added to a 250 mL single neck round bottom flask under an inert atmosphere. Oxalyl chloride (6.8 mL, 0.0779 mol) is added dropwise, followed by a catalytic amount of N,N-dimethylformamide (DMF, 0.30 µL, 3.87 mmol). The mixture was stirred for 30 min. until gas evolution is observed to cease. The mixture is then stirred for an additional 90 min before the solvent is removed by rotary evaporation to afford a viscous, pale yellow oil. The acid chloride compound thus obtained was used in the next step without further purification.

Step II—Synthesis of 5-(2'-decyltetradecanamido)-2-benzimidazolone

5-Aminobenzimidazolone (2.93 g, 19.6 mmol) and triethylamine (4 mL, 28.7 mmol) are dissolved in 20 mL of N-methylpyrrolidinone (NMP) in a 250 mL round bottom flask under an inert atmosphere. To this solution, a second solution of 2-decyltetradecanoyl chloride from Step I dissolved in dry THF (150 mL) is slowly added. After stirring overnight, deionized water is added and the mixture is poured in to 300 mL of ethyl acetate and washed with three 100 mL portions of deionized water. The organic layer is then concentrated by rotary evaporation until a white slurry is obtained. The solid is collected by filtration and washed with cold ethyl acetate to give 5-(2'-decyltetradecanamido)-2-benzimidazolone as a white solid (7.18 g). The product is identified by $^1$H and $^{13}$C NMR spectroscopy and ESI-MS and is of satisfactory purity.

Example 2

Gel formation from 5-(2'-decyltetradecanamido)-2-benzimidazolone (compound #2 (m=11, n=9), Table 1)

This example demonstrates that compound #2 (m=11, n=9) from Example 1 of the present invention forms organogels via hydrogen-bonding, van der Waals interactions, and π-π stacking interactions in appropriate organic solvents.

Compound #2 (m=11, n=9) from Example 1 and a solvent (1 mL) are added to a 1 dram vial and the mixture is sonicated and heated until a clear solution was formed. The hot solution is then cooled to room temperature and is allowed to stand for at least 30 minutes before inverting the sample vial. The sample did not flow, and is judged visually to be a gel.

The gelation ability of Compound #2 (m=11, n=9) for various solvents is listed in Table 3. Clear gels are formed in cyclic, aliphatic hydrocarbon solvents such as cyclohexane and decalin, while turbid gels are formed in 1,2-dichloroethane, and linear hydrocarbon solvents such as hexanes and dodecane. In hexanes and dodecane, the gels were observed to shrink over time resulting in partial phase separation of some of the liquid phase.

TABLE 3

| Solvent | Gelator Ability | Concentration (wt %) |
| --- | --- | --- |
| Chloroform | S | 1.0 |
| 1,2-dichloroethane | G | 0.8 |
| Cyclohexane | G | 6.3 |
| Decalin | G | 2.3 |
| Toluene | P | 2.1 |
| Xylenes | P | 2.0 |
| Hexanes | G | 3.1 |
| Dodecane | G | 2.9 |

S = Soluble
G = Gel
P = Precipitate
* = denotes turbid gel
** = denotes turbid gel that shrunk after several hours after gelation

Example 3

Synthesis of 5-(2'-hexyldecanamido)-2-benzmidazolone (compound #2 (m=7, n=5), Table 1)

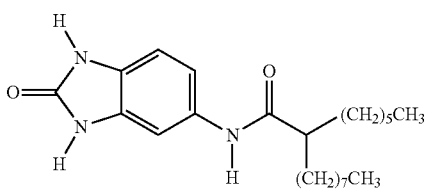

Step I—Synthesis of 2-hexyldecanoyl chloride

2-Hexydecanoic acid (Jaric acid, JARCHEM, 6.61 g, 0.0258 mol) and dry THF (50 mL) are added to a 250 mL single neck round bottom flask under an inert atmosphere. Oxalyl chloride (9.0 mL, 0.103 mol) is added slowly, dropwise, followed by a catalytic amount of DMF (0.30 mL, 3.87 mmol). The mixture is stirred for 30 min. until gas evolution is observed to cease. The mixture is then stirred for an additional 90 min. before the solvent is removed by rotary evaporation to afford a viscous mixture containing precipitates. The acid chloride compound thus obtained is used in the next step without further purification.

Step II—Synthesis of 5-(2'-hexyldecanamido)-2-benzmidazolone

5-Aminobenzimidazolone (3.86 g, 25.8 mmol) and triethylamine (5.4 mL, 38.7 mmol) are dissolved in 20 mL of N-methylpyrrolidinone (NMP) in a 250 mL round bottom flask under an inert atmosphere. To this solution, a second solution of 2-hexyldecanoyl chloride from Step I dissolved in dry THF (50 mL) is slowly added. After stirring overnight, deionized water is added and the mixture is poured in to 300 mL of ethyl acetate and washed with three 100 mL portions of deionized water. The organic layer is then concentrated by rotary evaporation until a white slurry is obtained. The solid is collected by filtration and washed with cold ethyl acetate to give 5-(2'-hexyldecanamido)-2-benzmidazolone as a white solid (6.37 g). The product is identified by $^1$H and $^{13}$C NMR spectroscopy and ESI-MS and is of satisfactory purity.

Example 4

Synthesis of 5-isostearylamido-2-benzimidazolone (compound #3 in Table 1)

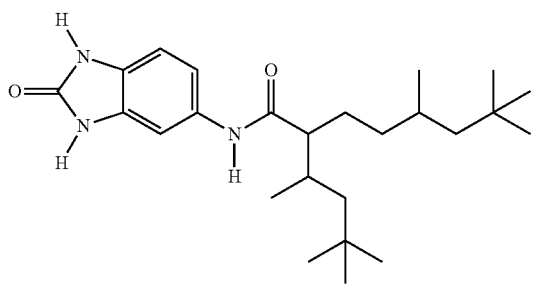 [SMILES: CC(CCC(C(=O)Nc1ccc2[nH]c(=O)[nH]c2c1)C(C)CC(C)(C)C)CC(C)(C)C]

Step I—Synthesis of Isostearoyl Chloride

Isostearic acid (Nissan chemical, 6.83 g, 24.0 mmol) and dry THF (50 mL) are added to a 250 mL single neck round bottom flask under an inert atmosphere. Oxalyl chloride (9.0 mL, 0.103 mol) is added slowly, dropwise, followed by a catalytic amount of DMF (0.350 mL, 4.52 mmol). The mixture is stirred for 30 min. until gas evolution is observed to cease. The mixture is then stirred for an additional 3 hr before the solvent is removed by rotary evaporation to afford viscous, pale yellow oil containing some white precipitates. The acid chloride compound thus obtained was used in the next step without further purification.

Step II—Synthesis of 5-isostearylamido-2-benzimidazolone

5-Aminobenzimidazolone (3.58 g, 24.0 mmol) and triethylamine (5 mL, 35.9 mmol) are dissolved in 40 mL of N-methylpyrrolidinone (NMP) in a 250 mL round bottom flask under an inert atmosphere. To this solution, a second solution of isostearoyl chloride from Step I dissolved in dry THF (50 mL) is slowly added. After stirring overnight, deionized water is added and the THF removed by rotary evaporation. The crude residue is then redissolved in 300 mL of ethyl acetate and is washed with three 100 mL portions of deionized water. The organic layer is then concentrated by rotary evaporation to afford 5-isostearylamido-2-benzimidazolone as a light beige solid (10.8 g). The product is identified by $^1$H and $^{13}$C NMR spectroscopy and ESI-MS and is of satisfactory purity.

Example 5

Synthesis of 5-isostearyl N amido-2-benzimidazolone (compound #4 in Table 1)

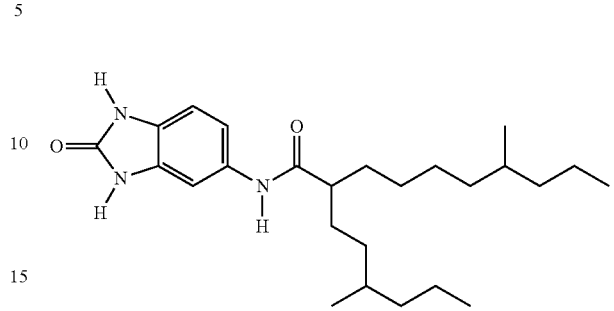

Step I—Synthesis of Isostearoyl N Chloride

Isostearic acid N (Nissan chemical, 1.37 g, 4.82 mmol) and dry THF (20 mL) are added to a 100 mL single neck round bottom flask under an inert atmosphere. Oxalyl chloride (0.850 mL, 9.74 mmol) is added slowly, dropwise, followed by 8 drops of DMF. The mixture is stirred for 30 min. until gas evolution is observed to cease. The mixture is then stirred for 2 hr before the solvent is removed by rotary evaporation to afford a yellow oil. The acid chloride compound thus obtained is used in the next step without further purification.

Step II—Synthesis of 5-isostearic N amido-2-benzimidazolone

5-Aminobenzimidazolone (0.730 g, 4.89 mmol) and triethylamine (1 mL, 7.17 mmol) are dissolved in 10 mL of N-methylpyrrolidinone (NMP) in a 250 mL round bottom flask under an inert atmosphere. To this solution, a second solution of isostearoyl N chloride from Step 1 dissolved in dry THF (30 mL) is slowly added. After stirring overnight, deionized water is added and the THF removed by rotary evaporation. The crude residue is then dissolved in 100 mL of ethyl acetate and is washed with three 50 mL portions of deionized water. The organic layer is then concentrated by rotary evaporation to afford 5-isostearic N amido-2-benzimidazolone as a light beige solid (2.04 g). The product is identified by $^1$H and $^{13}$C NMR spectroscopy and ESI-MS and is of satisfactory purity.

Example 6

Self-Assembled 1D Aggregates with Nanoscale Dimensions from Alkylated Benzimidazolone Compounds This example demonstrates that the alkylated benzimidazolone compounds of the present invention form colloidal solutions of nanoscale, self-assembled molecular assemblies through hydrogen-bonding, van der Waals interactions, and π-π stacking interactions in appropriate organic solvents.

1.0-2.0 mg of compounds 2, 3, and 5 from Table 1 are dissolved in 1 mL of toluene, xylenes, cyclohexanes, or hexanes with sonication and heating with a heat gun until clear solutions are obtained. After heating, the solutions are cooled to room temperature for at least 30 min. In some cases, the solid does not completely dissolve after heating. In other cases some precipitates are formed after the solutions are cooled to room temperature. Electron microscopy samples are prepared by depositing a drop of each mixture onto a carbon coated TEM grid, the excess is carefully wicked away using Whatman no. 1 filter paper and allowed to air dry. Table 4 summarizes the nanoscale supramolecular aggregates observed in SEM images for compounds 1, 2, 4, and 6 with the estimated dimensions.

TABLE 4

| Compound (Table 1) | Solvent | Concentration (mg/mL) | Solubility | Nanostructure Morphologies | Dimensions L (nm) | W (nm) |
|---|---|---|---|---|---|---|
| 2 (m = 7, n = 5) | Toluene | 0.9 | P | Rods | 500-6000 | 250-2000 |
|  |  |  |  | Nanofibrils | 100-500 | 10-30 |
|  | CHCl$_3$ | 1.0 | I | Nanofibers | 200-1000 | 40-160 |
| 1 (m = 11, n = 9) | Toluene | 2.0 | S | Rods | 400-4000 | 25-400 |
|  |  |  |  | Nanofibrils | 10-100 | 5-25 |
|  | Toluene | 1.0 | S | Nanofibrils | 50-200 | 5-25 |
|  | Xylenes | 1.0 | P | Nanofibrils | 50-200 | 5-25 |
|  | Cyclohexane | 1.0 | S | Nanofibers | 200-4000 | 30-50 |
|  |  |  |  | Nanofibrils | 5-25 | 5-10 |
| 3 | Hexanes | 1.1 | I | Nanofibers | 200-1000 | 15-40 |
|  |  |  |  | Nanofibrils | 100-300 | <10 |
|  | Xylenes | 1.1 | S | Nanofibers | 200-2000 | 10-50 |
|  |  |  |  | Nanofibrils | <100 | 5-10 |
|  | Toluene | 1.3 | P | Nanofibers | 100-10000 | 15-700 |
|  |  |  |  | Nanofibrils | 100-1000 | 5-10 |
| 4 | Toluene | 1.0 | S | Nanofibrils | 10-80 | 5-10 |

P = precipitates formed upon cooling
I = solid did not completely dissolve
S = solution Example 7

Synthesis of 5-dodecanamido-2-benzimdazolone (compound #1 (n=11), Table 1)

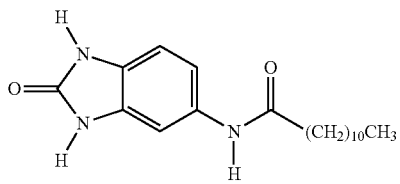

Step I—Synthesis of Lauroyl Chloride

Laurie acid (1.28 g, 6.39 mmol) and dry THF (20 mL) are added to a 100 mL single neck round bottom flask under an inert atmosphere. Oxalyl chloride (1.2 mL, 13.8 mmol) is added slowly, dropwise, followed by a catalytic amount of DMF (4 drops). The mixture was stirred for 30 min. until gas evolution is observed to cease. The mixture is then stirred for 90 min. before the solvent is removed by rotary evaporation and dried in vacuo. The acid chloride compound thus obtained was used in the next step without further purification.

Step II—Synthesis of 5-dodecanamido-2-benzimdazolone

5-Aminobenzimidazolone (0.95 g, 6.36 mmol), triethylamine (1.1 mL, 7.89 mmol), N-methylpyrrolidinone (NMP, 5 mL), and dry THE (8 mL) are mixed in a 100 mL round bottom flask under an inert atmosphere. To this solution, a second solution of 2-decyltetradecanoyl chloride from Step I dissolved in dry THE (30 mL) is slowly added. After stirring overnight, deionized water (50 mL) is added and the THF removed by rotary evaporation to give an aqueous slurry. The solid was collected by vacuum filtration and washed with deionized water before suspending in methanol (60 mL) and heating to reflux. The suspension was then cooled and the solid was filtered and washed with fresh methanol to give 5-dodecanamido-2-benzimdazolone as a white powder (1.63 g). The product is identified by $^1$H and $^{13}$C NMR spectroscopy and ESI-MS and is of satisfactory purity.

Example 8

Synthesis of bis-[5,5-(9',10'-dinonyloctadecanamido)-2-benzimidazolone] (compound 113, Table 2)

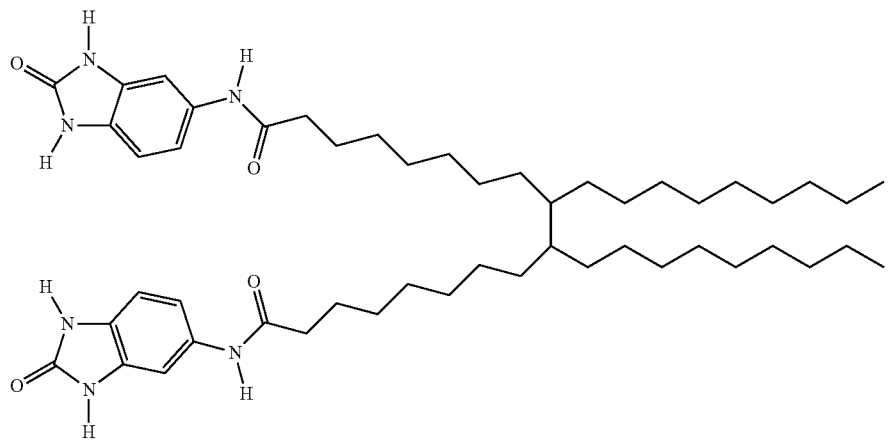 [SMILES: CCCCCCCCCC(CCCCCCCC(=O)Nc1ccc2[nH]c(=O)[nH]c2c1)C(CCCCCCCCC)CCCCCCCC(=O)Nc1ccc2[nH]c(=O)[nH]c2c1]

Step I—Synthesis of 9,10-dinonyloctadecanoyl dichloride 9,10-dinonyloctadecanoic acid (Pripol 1006, 3.44 g, 6.07 mmol) and dry THF (50 mL) are added to a 250 mL round bottom flask under an inert atmosphere and cooled to 0° C. Oxalyl chloride (3.20 mL, 36.7 mmol) is added slowly, dropwise, followed by DMF (0.140 mL, 1.81 mmol). The mixture is then slowly allowed to warm to room temperature and is stirred for 3.5 h. before the solvent is removed by rotary evaporation and dried in vacuo to give a pale yellow oil. The diacid chloride compound thus obtained was used in the next step without further purification.

Step II—Synthesis of bis-[5,5-(9',10'-dinonyloctadecanamido)-2-benzimidazolone]

5-Aminobenzimidazolone (1.92 g, 12.8 mmol), triethylamine (2.5 mL, 1789 mmol) and dry N-methylpyrrolidinone (NMP, 20 mL) are mixed in a 100 mL round bottom flask under an inert atmosphere. To this solution, a second solution of 9,10-dinonyloctadecanoyl dichloride from Step I dissolved in dry THF (50 mL) is slowly added. After stirring overnight, deionized water (50 mL) is added to the beige suspension and the solid was collected by vacuum filtration and washed with deionized water to give bis-[5,5-(9',10'-dinonyloctadecanamido)-2-benzimidazolone] (compound 3, Table 3) as a beige powder (4.87 g). The product is identified by $^1$H and $^{13}$C NMR spectroscopy and ESI-MS and is of satisfactory purity.

Example 9

Synthesis of 5-(didodecylamino)-2-benzimidazolone (compound #7 (n=11), Table 1)

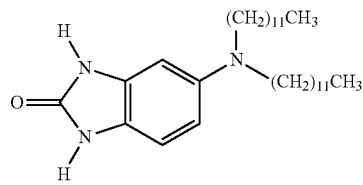

5-Aminobenzimidazolone (0.1348 g, 0.904 mmol), potassium iodide (0.1513 g, 0.911 mmol), and dry DMF (20 mL) are mixed in a 100 mL round bottom flask under an inert atmosphere. The reaction is heated to 60° C. and 1-bromododecane (0.45 mL, 1.88 mmol) is added. After 3 days at 60° C., the reaction is cooled to room temperature to give a brown suspension. The solid is filtered, washed with deionized water, and dried in vacuo to give 5-(didodecylamino)-2-benzimidazolone as a white solid (0.334 g). The product is identified by $^1$H and $^{13}$C NMR spectroscopy and ESI-MS and is of satisfactory purity.

Example 10

Synthesis of 5-n-stearylureido-2-benzimidazolone (compound #5, Table 1)

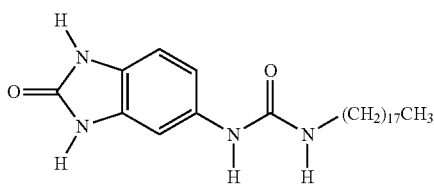

5-Aminobenzimidazolone (0.68 g, 4.6 mmol) is dissolved in of dry DMF (20 mL) in a 100 mL round bottom flask under an inert atmosphere. With stirring, the solution is then cooled to 0° C. before a 0.42 M solution of octadecylisocyanate (4.9 mmol) in dry DMF (10 mL) is added dropwise, which results in a white suspension. The mixture is slowly allowed to warm to room temperature and stirred for 67 h before the solid is filtered, washed with methanol, and dried in vacuo to afford 5-n-stearylureido-2-benzimidazolone as a grayish-white powder (1.94 g). The product is identified by $^1$H NMR spectroscopy and is of satisfactory purity.

Example 11

Self-assembled nanofibers from 5-n-stearylureido-2-benzimidazolone (compound #5, Table 1) of Example 10 in 1-hexanol 5-n-stearylureido-2-benzimidazolone (compound #5, Table 1, 1.3 mg, 3.01 µmol) is dissolved in 1-hexanol (1 mL) with heating using a heat gun until a clear solution is obtained. Upon cooling to room temperature, a precipitate forms which eventually settles. The settled solid is redispersed with agitation (shaking) and a droplet is deposited onto a carbon film coated TEM grid, the excess liquid is carefully wicked away using filter paper, and the sample is allowed to air dry. SEM images of the deposited solid show large nanofiber aggregates, whose widths range from 75 to 400 nm, and lengths from 50 to 10 µm.

Example 12

Self-assembled nanostructures from 5-n-stearylureido-2-benzimidazolone (compound #5, Table 1) of Example 10 in DMSO 1.2 mg of 5-n-stearylureido-2-benzimidazolone of Example 3 (3.01 µmol) is dissolved in 1 mL of DMSO with heating with a heat gun until a clear solution is obtained. Upon cooling to room temperature, a precipitate forms, which eventually settles. The settled solid is redispersed with agitation (shaking) and a droplet was deposited onto a carbon film coated TEM grid, the excess liquid is carefully wicked away using filter paper, and the sample is allowed to air dry. SEM images of the deposited solid showed pseudo-spherical, flower shaped particles with diameters ranging between 5-50 µm. Images taken at higher magnifications clearly show lamellar and rod-like nanofeatures. The lamellar folds are 10-50 nm thick while the rod-like features are ~50 nm wide.

Example 13

Self-Assembled Nanofibers from Acetoacetyl-5-Aminobenzimidazolone in Water

This example describes a procedure for producing nanofibers from a commercially available 5-acetoacetylated 5-aminobenzimidazolone derivative.

11.4 mg of acetoacetyl-5-aminobenzimidazolone (TCI America, 48.9 µmol) is dissolved in 0.92 mL of aqueous 0.1 M NaOH. 10 µL of concentrated glacial acetic acid is then added and a thick white precipitate is formed. The suspension is then diluted with 9 mL of deionized water and briefly sonicated in an ultrasonic bath. A droplet is deposited onto a carbon film coated TEM grid, the excess liquid is carefully wicked away using filter paper, and the sample is allowed to air dry. STEM analysis of the sample clearly showed nanofiber aggregates with uniform widths between 9 and 15 nm with lengths ranging between 75 to 350 nm.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. An alkylated benzimidazolone compound selected from the group consisting of the following compounds:

TABLE 1

| Position 5 functional moiety | X | Sterically Bulky Group(s) $R_1$ |
|---|---|---|
| –X–C(O)–$R_1$ | NH | $(CH_2)_nCH_3$, n = 11, 17 |
| –X–C(O)–$R_1$ | NH | branched: $(CH_2)_mCH_3$ / $(CH_2)_nCH_3$; m = 5, n = 3; m = 7, n = 5; m = 11, n = 9 |
| –X–C(O)–$R_1$ | NH | (highly branched alkyl) |
| –X–C(O)–$R_1$ | NH | (branched alkyl) |
| –$X_1$–C(O)–$X_2$–$R_1$ | $X_1$ = NH, $X_2$ = NH | $(CH_2)_nCH_3$, n = 11, 17 |
| –$X_1$–C(O)–$X_2$–$R_1$ | $X_1$ = O, $X_2$ = NH | $(CH_2)_nCH_3$, n = 11, 17 |
| –X(–$R_1$)–$R_2$ | N | H |

TABLE 1-continued

| Position 5 functional moiety | X | Sterically Bulky Group(s) $R_1$ |
|---|---|---|
| –X(–$R_1$)–$R_2$ | N | H |
| –X(–$R_1$)–$R_2$ | N | $(CH_2)_nCH_3$, n = 3, 11, 17 |
| –X(–$R_1$)–$R_2$ | N | –CH(CH_3)–(O–)$_n$(CH_2)_mCH_3; m = 3, n = 2; m = 3, n = 3 |
| –X(–$R_1$)–$R_2$ | N | –CH_2CH_2(O–)$_n$(CH_2)_mCH_3; m = 1, n = 3 |
| –X$^{\oplus}$(–$R_1$)(–$R_2$)–$R_3$ | N | $(CH_2)_nCH_3$, n = 1, 17 |
| –X$^{\oplus}$(–$R_1$)(–$R_2$)–$R_3$ | N | –CH(CH_3)–(O–)$_n$(CH_2)_mCH_3; m = 3, n = 2; m = 3, n = 3 |
| –X$^{\oplus}$(–$R_1$)(–$R_2$)–$R_3$ | N | –CH_2CH_2(O–)$_n$(CH_2)_mCH_3; m = 1, n = 3 |

| Position 5 functional moiety | Sterically Bulky Group(s) $R_2$ | $R_3$ |
|---|---|---|
| –X–C(O)–$R_1$ | — | — |
| –X–C(O)–$R_1$ | — | — |
| –X–C(O)–$R_1$ | — | — |
| –X–C(O)–$R_1$ | | |

TABLE 1-continued

| Structure | Col A | Col B |
|---|---|---|
| benzimidazolone-5-yl (NH, C=O, NH) | — | — |
| ~X-C(=O)-R₁ | — | — |
| ~X₁-C(=O)-X₂-R₁ | — | — |
| ~X₁-C(=O)-X₂-R₁ | — | — |
| ~X(R₂)(R₁) | (CH₂)ₙCH₃  n = 1, 17 | — |
| ~X(R₂)(R₁) | ~(O)ₙ(CH₂)ₘCH₃  m = 3, n = 2  m = 3, n = 3 | — |
| ~X(R₂)(R₁) | (CH₂)ₙCH₃  n = 3, 11, 17 | — |
| ~X(R₂)(R₁) | ~(O)ₙ(CH₂)ₘCH₃  m = 3, n = 2  m = 3, n = 3 | — |
| ~X(R₂)(R₁) | ~(O)ₙ(CH₂)ₘCH₃  m = 1, n = 3 | — |
| ~X⁺(R₃)(R₂)(R₁) | (CH₂)ₙCH₃  n = 1, 17 | (CH₂)ₙCH₃  n = 1, 17 |
| ~X⁺(R₃)(R₂)(R₁) | ~(O)ₙ(CH₂)ₘCH₃  m = 3, n = 2  m = 3, n = 3 | ~(O)ₙ(CH₂)ₘCH₃  m = 3, n = 2  m = 3, n = 3 |

TABLE 1-continued

| Structure | Col A | Col B |
|---|---|---|
| benzimidazolone-5-yl (NH, C=O, NH) | | |
| ~X⁺(R₃)(R₂)(R₁) | ~(O)ₙ(CH₂)ₘCH₃  m = 1, n = 3 | ~(O)ₙ(CH₂)ₘCH₃  m = 1, n = 3 |

TABLE 2

$R_a, R_b$ on benzimidazolone N; $X{-}_2 R_c$ at 5-position $R_a = R_b = H$

Group X

~X₁-C(=O)-X₂~
$X_1 = X_2 = NH$

~X₁-C(=O)-X₂~
$X_1 = O$
$X_2 = NH$

~X₁-C(=O)-~
$X_1 = NH$

~X₁-C(=O)-~
$X_1 = O$ (CH₃)₂C-C(=O)-X₁~
$X_1 = O$ (CH₃)₂C-C(=O)-X₁~
$X_1 = NH$

TABLE 2-continued

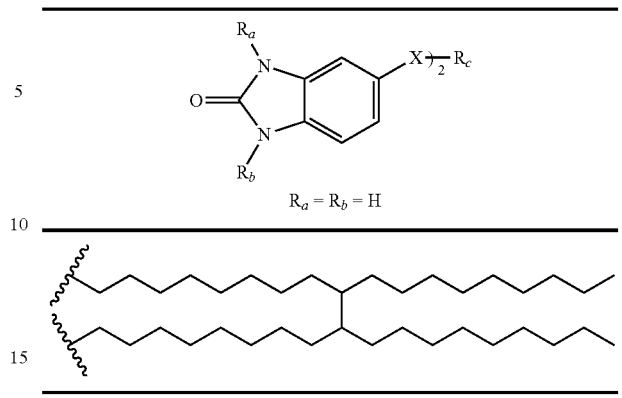

$R_a = R_b = H$

| $R_c$ |
|---|
| 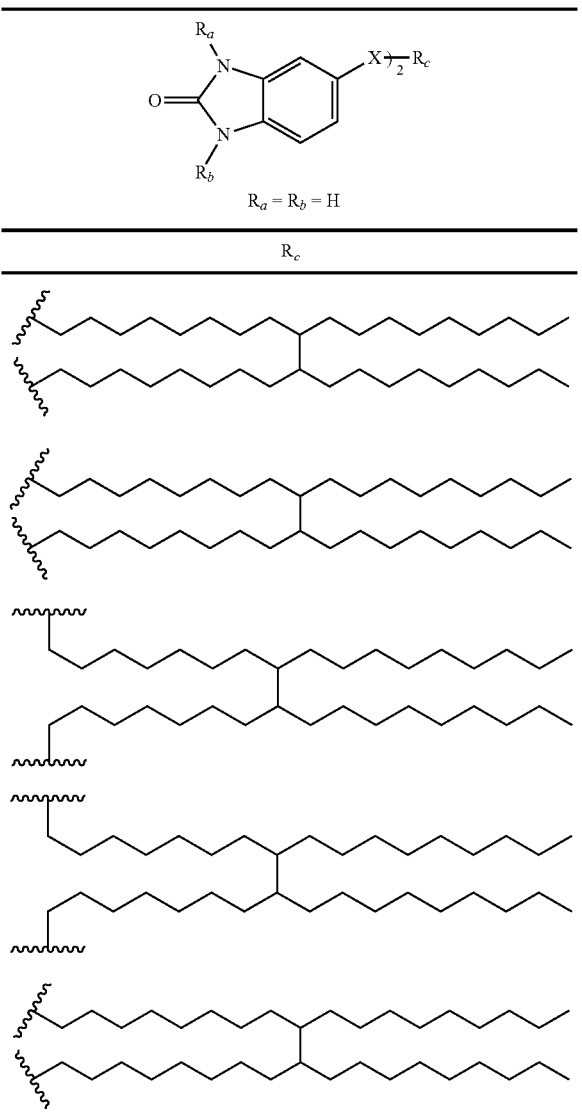 |

TABLE 2-continued

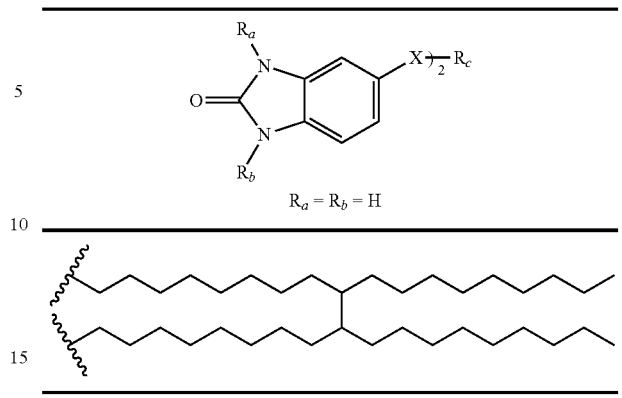

$R_a = R_b = H$ and mixtures thereof.

2. A nanostructure comprising molecules of the compound according to claim 1, non-covalently bound to each other.

3. The nanostructure of claim 2, wherein the non-covalent bonding is predominately through hydrogen-bonding, aromatic pi-pi interactions, and van der Waals' forces.

4. The nanostructure of claim 2, wherein the nanostructure is formed by homogeneously mixing the compound with a polar or nonpolar liquid under conditions to effect dissolution and self-assembly of the compound.

5. The nanostructure of claim 2, wherein the nanostructure is a one-dimensional structure in the form of a nanofibril or nanofiber.

6. The nanostructure of claim 2, wherein the nanostructure is a two-dimensional structure.

7. The nanostructure of claim 2, wherein the nanostructure is a three-dimensional structure in the form of a non-covalent gelator network or gel.

8. The nanostructure of claim 2, wherein the nanostructure has, in at least one dimension, a size ranging from about 1 to about 500 nm, and has a largest dimension of up to about 5000 nm.

9. A marking material composition comprising the nanostructure of claim 2, wherein the marking material is an ink, a toner, a developer, a paint, or a coating.

10. An organogel composition comprising the nanostructure of claim 2.

* * * * *